US012810999B2

(12) United States Patent
Sasai et al.

(10) Patent No.: US 12,810,999 B2
(45) Date of Patent: Nov. 24, 2026

(54) LEARNING SUPPORT DEVICE, ENDOSCOPE SYSTEM, METHOD FOR SUPPORTING LEARNING, AND RECORDING MEDIUM

(71) Applicant: OLYMPUS CORPORATION, Tokyo (JP)

(72) Inventors: Ryota Sasai, Tokyo (JP); Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 313 days.

(21) Appl. No.: 18/614,942

(22) Filed: Mar. 25, 2024

(65) Prior Publication Data

US 2024/0331847 A1 Oct. 3, 2024

Related U.S. Application Data

(60) Provisional application No. 63/455,045, filed on Mar. 28, 2023.

(51) Int. Cl.

*G16H 30/40* (2018.01)
*G06T 5/50* (2006.01)

(Continued)

(52) U.S. Cl.

CPC ............... *G16H 30/40* (2018.01); *G06T 5/50* (2013.01); *G06T 7/194* (2017.01); *G06T 7/70* (2017.01);

(Continued)

(58) Field of Classification Search

CPC ........... G16H 30/40; G06T 7/194; G06T 7/70; G06T 5/50; G06T 2207/10068;

(Continued)

(56) References Cited

U.S. PATENT DOCUMENTS 7,791,651 B2 9/2010 Donomae et al.
8,882,662 B2 * 11/2014 Charles ................ A61B 1/0004 600/210

(Continued)

FOREIGN PATENT DOCUMENTS

DE 102019132045 A1 * 5/2020 ........... H04N 23/555
EP 1650708 A1 4/2006

(Continued)

OTHER PUBLICATIONS

Jin Yueming et al. "Incorporating Temporal Prior from Motion Flow for Instrument Segmentation in Minimally Invasive Surgery Video", Jul. 18, 2019, arXiv (Year: 2019).*

(Continued)

*Primary Examiner* — John Villecco
*Assistant Examiner* — Alejandro Hernandez
(74) *Attorney, Agent, or Firm* — Scully, Scott, Murphy & Presser, P.C.

(57) ABSTRACT

A learning support device includes a processor. The processor is configured to: form a foreground image containing at least one treatment instrument by placing an image of the at least one treatment instrument within an image region based on placement data; and form a training image by superimposing the foreground image on a background image. The placement data are data showing a three-dimensional placement of the at least one treatment instrument as viewed through an endoscope.

12 Claims, 26 Drawing Sheets

(51) Int. Cl.
*G06T 7/194* (2017.01)
*G06T 7/70* (2017.01)
*G06V 10/25* (2022.01)
*G06V 10/60* (2022.01)

(52) U.S. Cl.
CPC .............. *G06V 10/25* (2022.01); *G06V 10/60* (2022.01); *G06T 2207/10068* (2013.01); *G06T 2207/20221* (2013.01); *G06T 2207/30242* (2013.01)

(58) Field of Classification Search
CPC . G06T 2207/20221; G06T 2207/30242; G06T 7/50; G06T 7/0002; G06T 7/0012; G06T 19/006; G06T 15/08; G06V 10/25; G06V 10/60; G06V 10/774; G06V 10/20; G06V 20/40; A61B 1/00; A61B 1/00009; A61B 1/000096; A61B 1/00002; A61B 34/20; A61B 1/00004; A61B 1/000094; A61B 1/04; A61B 34/10; G09B 23/285
See application file for complete search history.

(56) References Cited

U.S. PATENT DOCUMENTS 10,614,346 B2 4/2020 Inoue
11,334,992 B2 * 5/2022 Schmidt-Richberg ........................ G06F 18/22
11,450,079 B2 9/2022 Usuda
11,451,698 B2 * 9/2022 Kikuchi ............... A61B 1/0005
12,272,034 B2 * 4/2025 Agarwal ................. G06T 7/194
12,300,386 B2 * 5/2025 Usuda ........................ G06T 7/11
12,582,288 B2 * 3/2026 Charles ................ A61B 1/0004
12,602,789 B2 * 4/2026 Zeng ......................... G06T 7/12
2010/0295931 A1 * 11/2010 Schmidt ................. A61B 34/20 345/633
2014/0005555 A1 * 1/2014 Tesar ................... A61B 1/0004 600/476
2015/0051617 A1 * 2/2015 Takemura ................ A61B 6/12 606/130
2016/0350912 A1 * 12/2016 Koide ................ G02B 23/2484
2019/0087694 A1 3/2019 Inoue
2020/0082229 A1 3/2020 Inoue
2020/0175343 A1 6/2020 Inoue
2020/0258235 A1 * 8/2020 Lu ......................... G06T 7/0012
2020/0285876 A1 * 9/2020 Usuda .............. A61B 1/000094
2020/0372668 A1 11/2020 Lin et al.
2021/0209398 A1 * 7/2021 Endo ..................... G06T 7/0012
2021/0319539 A1 * 10/2021 Agarwal ................... G06T 5/75
2022/0172828 A1 * 6/2022 Qiu ........................ G06T 7/0014
2022/0245800 A1 * 8/2022 Champagne ......... G06V 10/774
2022/0383607 A1 12/2022 Usuda
2023/0009051 A1 * 1/2023 Goto ...................... G06T 7/0012
2024/0055126 A1 * 2/2024 Wujek ................... G06N 3/082
2024/0161035 A1 * 5/2024 Lyman ................. A61B 5/7264
2024/0242351 A1 * 7/2024 Kusu ......................... G06T 7/11
2024/0274274 A1 8/2024 Usuda
2024/0331337 A1 * 10/2024 Lyu ........................ G06V 10/25
2024/0371060 A1 * 11/2024 Buschle .................. G06T 7/194
2025/0209616 A1 * 6/2025 Peles Zeevi ........... G16H 30/40
2026/0007302 A1 * 1/2026 Takenouchi ..... A61B 1/000094
2026/0051392 A1 * 2/2026 Themelis ................ G06T 7/215

FOREIGN PATENT DOCUMENTS

JP 2012120702 A * 6/2012
WO 2019/058300 A1 3/2019
WO 2020242572 A1 12/2020

OTHER PUBLICATIONS

Ruofeng; Wei et al. "Real-Time Monocular 2-D and 3-D Perception of Endoluminal Scenes for Controlling Flexible Robotic Endoscopic Instruments" Mar. 2026, IEEE (Year: 2026).*
Y. Mochizuki, "CV & Technologies_Normalizeimage brightness", Retrieved from the Internet, Mar. 31, 2017, URL:https://cvtech.cc/std/.
U.S. Appl. No. 18/614,838.
US Office Action dated Nov. 28, 2025 received in U.S. Appl. No. 18/614,838.

* cited by examiner

LEARNING SUPPORT DEVICE, ENDOSCOPE SYSTEM, METHOD FOR SUPPORTING LEARNING, AND RECORDING MEDIUM

CROSS-REFERENCE TO RELATED APPLICATIONS

This application claims the benefit of U.S. Provisional Application No. 63/455,045, filed Mar. 28, 2023, which is incorporated by reference herein in its entirety.

TECHNICAL FIELD

The present invention relates to a learning support device, an endoscope system, a method for supporting learning, and a recording medium.

BACKGROUND ART

In an endoscope system, a technique to automatically recognize treatment instruments within an endoscopic image is used. An example of a technique to recognize treatment instruments includes a method that uses deep learning, and deep learning requires a large number of training images.

There is also a known technique to form a training image from two images. For example, U.S. Pat. No. 10,614,346 discloses that intensities of respective pixels in a first image and a second image are simply averaged to form a training image.

SUMMARY OF THE INVENTION

One aspect of the present invention is a learning support device that supports formation of a learning model that recognizes a treatment instrument within an endoscopic image, the learning support device including a processor, wherein the processor is configured to: form a foreground image containing at least one treatment instrument by placing an image of the at least one treatment instrument within an image region based on placement data, the placement data being data showing a three-dimensional placement of the at least one treatment instrument as viewed through an endoscope; and form a training image by superimposing the foreground image on a background image.

Another aspect of the present invention is an endoscope system including: the above-mentioned learning support device; an endoscope configured to acquire an endoscopic image; and an image processing apparatus including a processor and a storage unit configured to store the learning model, wherein the processor of the image processing apparatus is configured to input the endoscopic image to the learning model to obtain, from the learning model, a recognition result with respect to the treatment instrument within the endoscopic image.

Another aspect of the present invention is a method for supporting learning, the method supporting formation of a learning model that recognizes a treatment instrument within an endoscopic image, the method including: forming a foreground image containing at least one treatment instrument by placing an image of the at least one treatment instrument within an image region based on placement data, the placement data being data showing a three-dimensional placement of the at least one treatment instrument as viewed through an endoscope; and forming a training image by superimposing the foreground image on a background image.

Another aspect of the present invention is a computer readable non-transitory recording medium that stores a learning support program that causes a computer to perform the above-mentioned method for supporting learning.

DETAILED DESCRIPTION OF THE INVENTION

First Embodiment

A learning support device and a method for supporting learning according to a first embodiment of the present invention will be described with reference to drawings.

A learning support device 10 according to the present embodiment supports formation of a learning model that recognizes treatment instruments within an endoscopic image. To be more specific, the learning support device 10 forms training images necessary to form a learning model.

Figure 1:
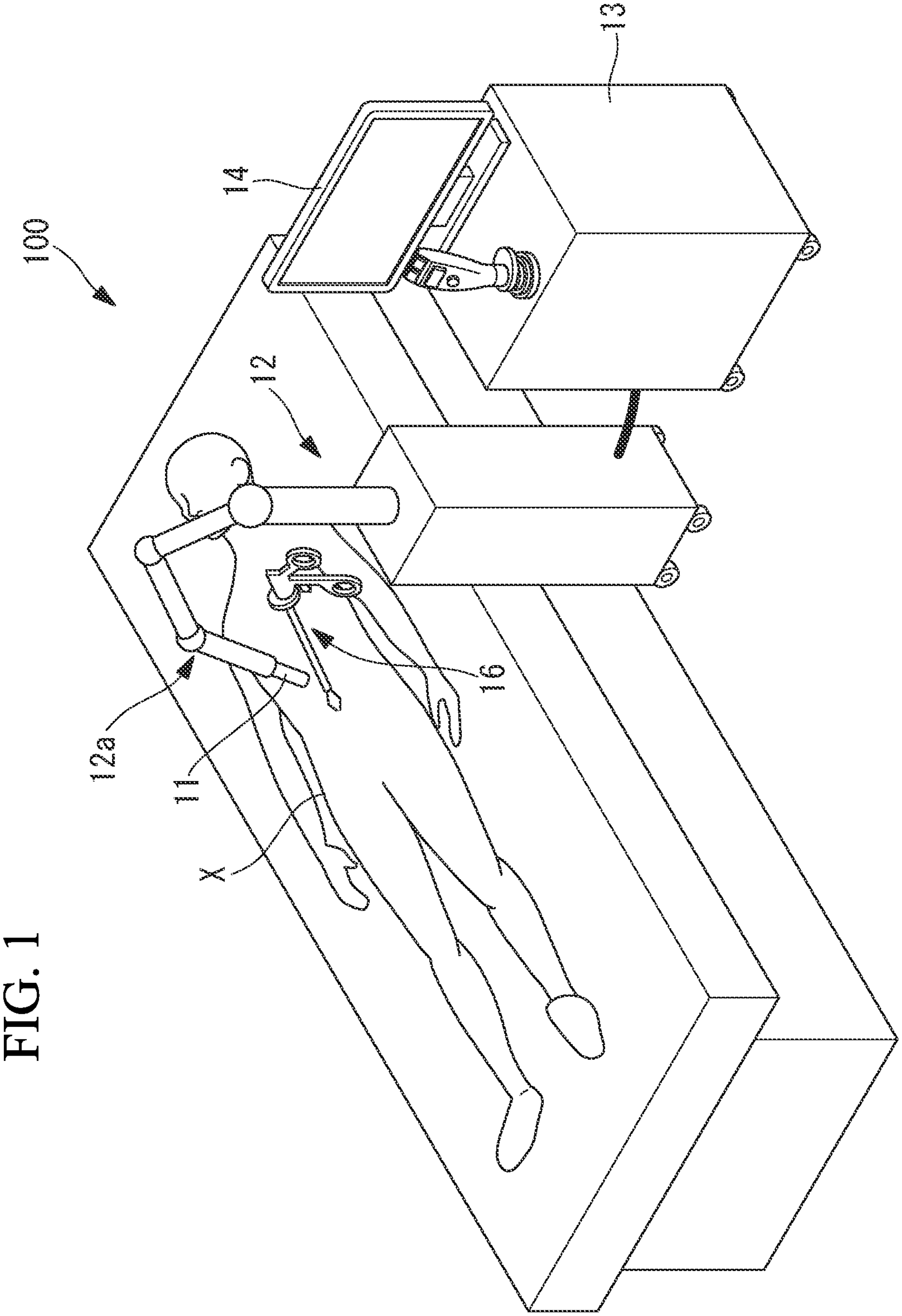
FIG. 1 is an overall configuration diagram showing an example of an endoscope system in which a learning support device is used.

FIG. 1 shows an example of an endoscope system 100 in which a learning model formed by the learning support device 10 is used. The endoscope system 100 includes an endoscope 11, a moving device 12 that changes a position and a orientation of the endoscope 11, a control device 13, and a display device 14. The endoscope system 100 is used for surgery in which the endoscope 11 and a treatment instrument 16 are inserted into a body of a patient as a subject X to treat a part to be treated with the treatment instrument 16 while the treatment instrument 16 is observed by the endoscope 11. For example, the endoscope system 100 is used for laparoscopic surgery.

Figure 2A:
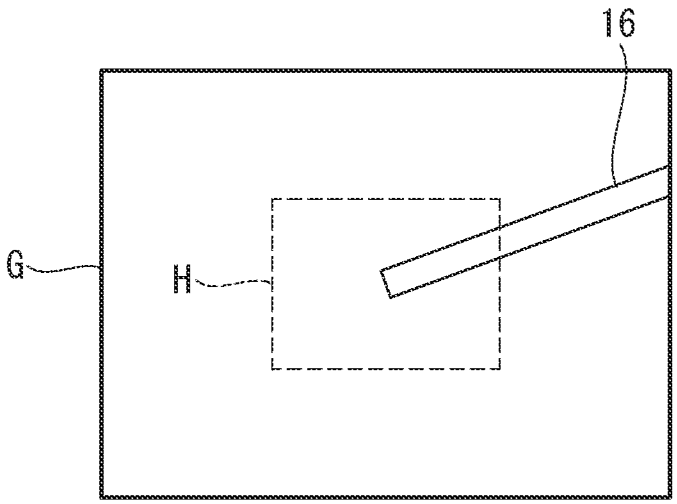
FIG. 2A is a diagram showing an endoscopic image to illustrate tracking control.
Figure 2B:
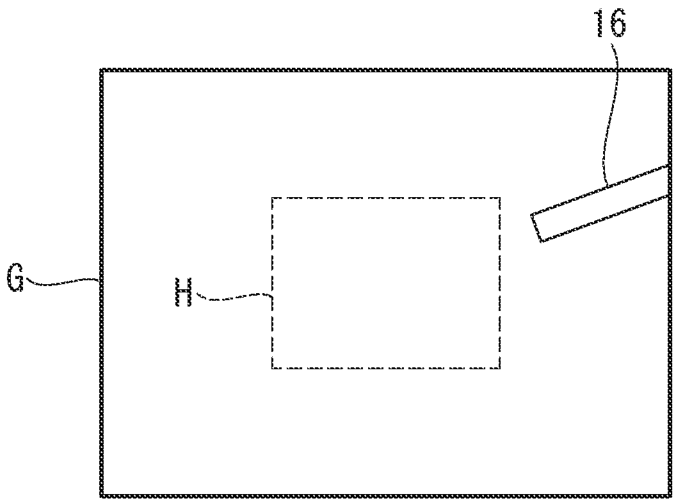
FIG. 2B is a diagram showing an endoscopic image to illustrate the tracking control.

The control device 13 performs tracking control that causes a field of view of the endoscope 11 to track the treatment instrument 16 by controlling the moving device 12 based on a position of the treatment instrument 16. FIG. 2A and FIG. 2B show examples of the tracking control. In these examples, the moving device 12 is controlled such that a distal end of the treatment instrument 16 is placed within a predetermined specified region H within an endoscopic image G. That is, when the distal end is located within the specified region H, the endoscope 11 is not moved (see FIG. 2A). In contrast, when the distal end is located outside the specified region H, the endoscope 11 is moved in such a way as to cause the distal end to be within the specified region H (see FIG. 2B).

The learning model is used to recognize the treatment instrument 16 as the target to be tracked within the endoscopic image G during tracking control, for example.

Figure 3:
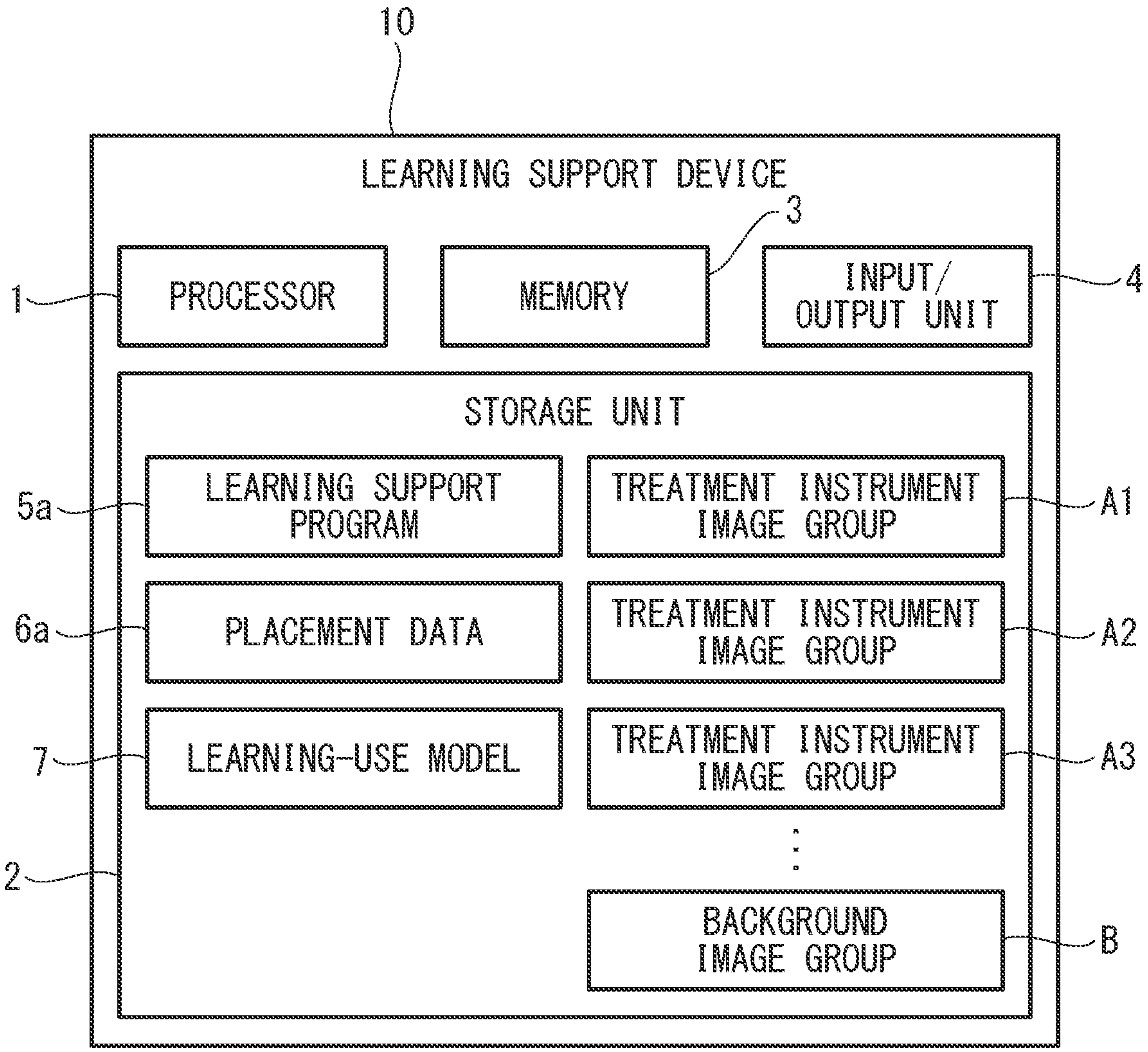
FIG. 3 is a block diagram showing a configuration of the learning support device according to a first embodiment.

As shown in FIG. 3, the learning support device 10 includes a processor 1, such as a central processing unit, a storage unit 2, a memory 3, and an input/output unit 4.

The storage unit 2 is a computer readable non-transitory recording medium, and may be a hard disk drive, an optical disk, or a flash memory, for example. The storage unit 2 stores a learning support program 5*a* that causes the processor 1 to perform a method for supporting learning according to the present embodiment, which will be described later. The storage unit 2 further stores sample image groups A1, A2, A3, . . . , B and placement data 6*a*, all of which are necessary for the method for supporting learning.

The processor 1 forms a training image D from the sample image groups A1, A2, A3, . . . , B according to the learning support program 5*a* that is read into the memory 3, such as a RAM (random access memory), from the storage unit 2.

The input/output unit 4 has a known input interface and a known output interface.

The sample image groups A1, A2, A3, . . . , B are images of objects that may appear in a clinical image. The clinical image is an endoscopic image acquired by the endoscope 11 during actual endoscopic surgery. In the present embodiment, sample image groups include a plurality of treatment instrument image groups A1, A2, A3, . . . , and a background image group B.

Each of the treatment instrument image groups A1, A2, A3, . . . is formed of a plurality of treatment instrument images containing treatment instrument 16*a*, 16*b*, 16*c*, . . . , and the treatment instruments 16*a*, 16*b*, 16*c*, . . . differ from each other.

The plurality of treatment instrument images of the treatment instrument image group A1 are a plurality of color images that differ from each other in distance in a depth direction (that is, size) and posture of the treatment instrument 16*a*. For example, the plurality of treatment instrument images are obtained by photographing, by an endoscope, the treatment instrument 16*a* placed on an arbitrary background at various distances and in various postures. In the same manner, the plurality of treatment instrument images of each of other treatment instrument image groups A2, A3, . . . are also a plurality of color images that differ from each other in distance and posture of the treatment instrument 16*b*, 16*c*, . . . .

The background image group B is formed of a plurality of color background images that differ from each other. A background image is an image of an organ, and is obtained by photographing various positions in an abdominal cavity at various angles by the endoscope, for example.

The placement data 6*a* are data showing three-dimensional placement of at least one treatment instrument as viewed through the endoscope, and includes distance information relating to a distance from the endoscope to each of at least one treatment instrument. The placement data 6*a* are created based on three-dimensional placement that may actually occur during endoscopic surgery with respect to the treatment instruments within a clinical image.

Figure 4:
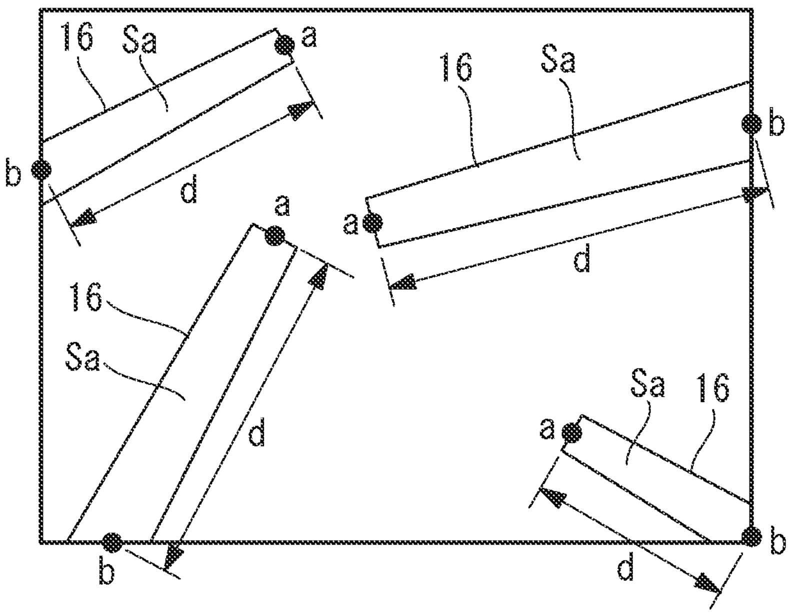
FIG. 4 is a diagram showing an example of placement data relating to treatment instruments.

FIG. 4 shows an example of the placement data 6*a*. The placement data 6*a* are image data including at least one treatment instrument 16, and include information on the number of treatment instruments 16, and the kind of, the positions of a distal end a and a proximal end b of, and an area Sa of each of the treatment instruments 16 in the endoscopic image. A length d of the treatment instrument 16 from the distal end a to the proximal end b and the area Sa correlate with the distance from the endoscope to the treatment instrument 16, and a shorter distance causes a larger length d and a larger area Sa. In the present embodiment, distance information includes the length d and the area Sa.

The placement of the treatment instruments that may occur during endoscopic surgery is constrained by conditions of endoscopic surgery, such as a surgical method, so that the number of patterns of placement is finite. A large number of sets of placement data 6*a* are prepared covering all placements that may occur during endoscopic surgery with respect to the treatment instruments. For example, thousands of sets of placement data 6*a* or more are prepared.

FIG. 5A to FIG. 6B illustrate examples of a method for creating the placement data 6*a*.

Figure 5A:
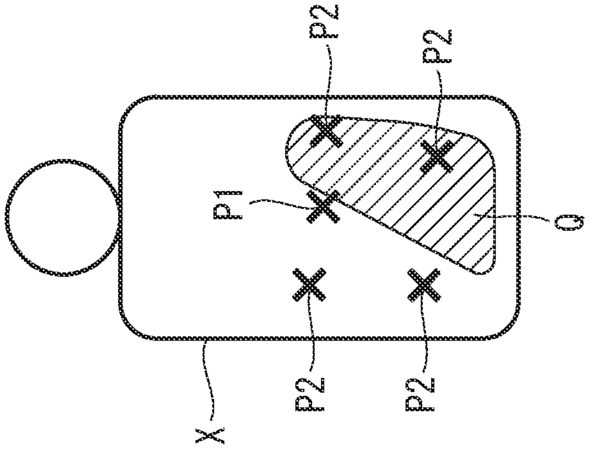
FIG. 5A is a diagram showing an example of an observation range and placement of an endoscope port and treatment instrument ports during laparoscopic surgery.
Figure 5B:
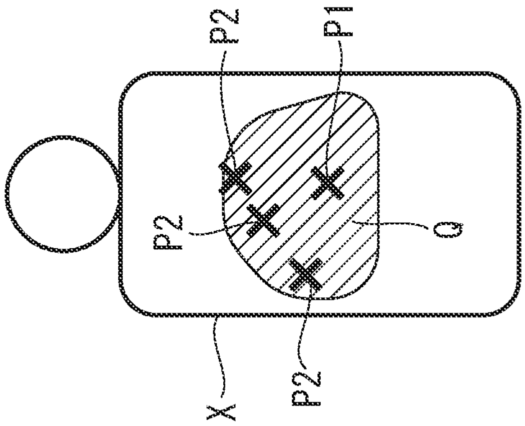
FIG. 5B is a diagram showing another example of the observation range and the placement of the endoscope port and the treatment instrument ports during laparoscopic surgery.
Figure 5C:
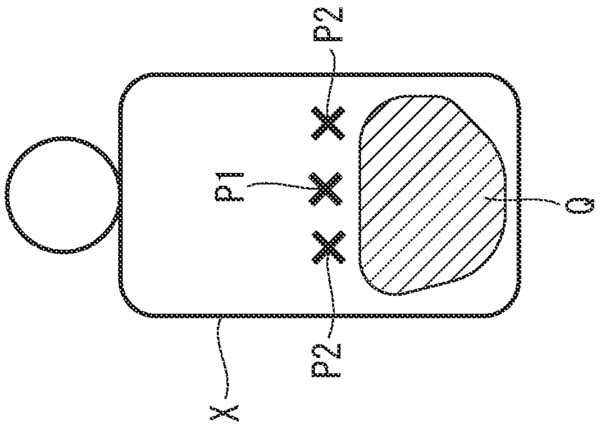
FIG. 5C is a diagram showing another example of the observation range and the placement of the endoscope port and the treatment instrument ports during laparoscopic surgery.
Figure 6A:
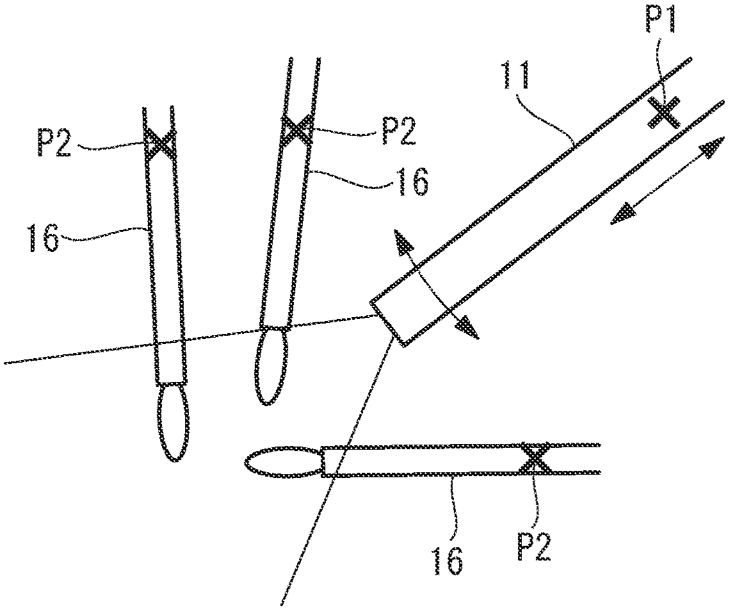
FIG. 6A is a diagram showing a three-dimensional positional relationship between treatment instruments and an endoscope in an abdominal cavity.

As shown in FIG. 5A to FIG. 5C, placement of an endoscope port P1 and treatment instrument ports P2, and a position of an observation range Q, in an abdominal cavity, observed by the endoscope 11 are determined for each surgical method of laparoscopic surgery. FIG. 5A, FIG. 5B, and FIG. 5C respectively show sigmoidectomy, cholecystectomy, and transabdominal preperitoneal repair. As shown in FIG. 6A, the endoscope 11 and the treatment instruments 16 are respectively inserted into the abdominal cavity from the ports P1, P2 provided to the abdominal wall of a patient X.

Figure 6B:
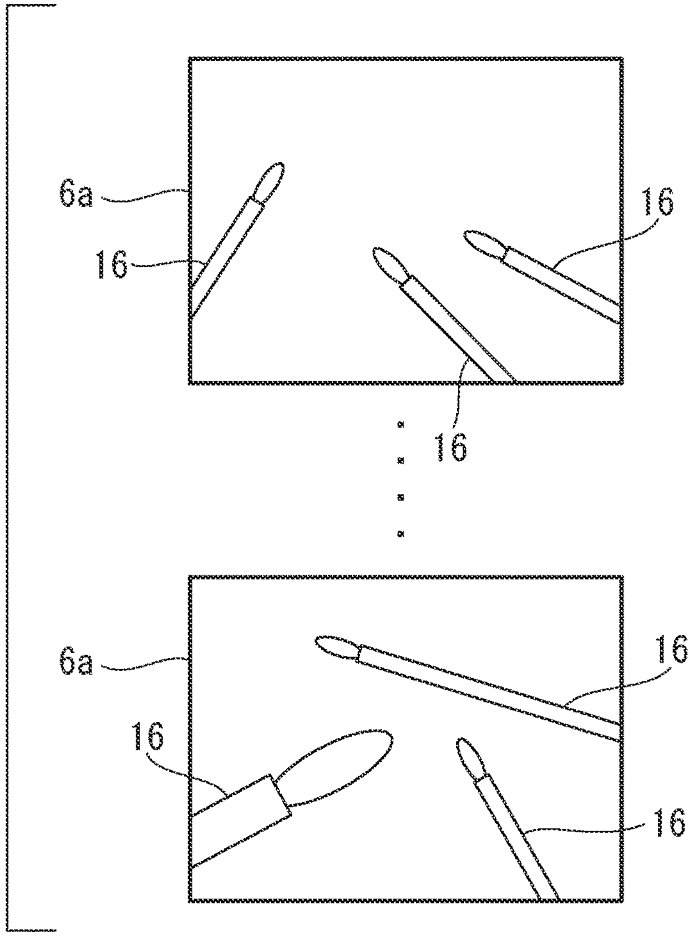
FIG. 6B is a diagram showing placement data created based on the positional relationship shown in FIG. 6A.

The movement of the endoscope 11 and the treatment instruments 16 is limited to swinging about the ports P1, P2 and to movement in a longitudinal direction and hence, the three-dimensional position and orientation that each of the treatment instruments 16 may take with respect to the distal end of the endoscope 11 are limited within a certain range that is determined by the placement of the ports P1, P2 and the observation range Q. Accordingly, the range of the number of treatment instruments 16 within a clinical image, and the ranges of the position and the orientation of each treatment instrument 16 within a clinical image are determined by a surgical method. As shown in FIG. 6B, by comprehensively changing the position and the orientation of each treatment instrument 16 with respect to the distal end of the endoscope 11 within the above-mentioned certain range, a large number of sets of placement data 6*a* are created covering the number of treatment instruments within the clinical image, and covering the positions a, b and the areas Sa of the treatment instruments within the clinical image.

Next, the method for supporting learning that is performed by the learning support device 10 will be described.

Figure 7:
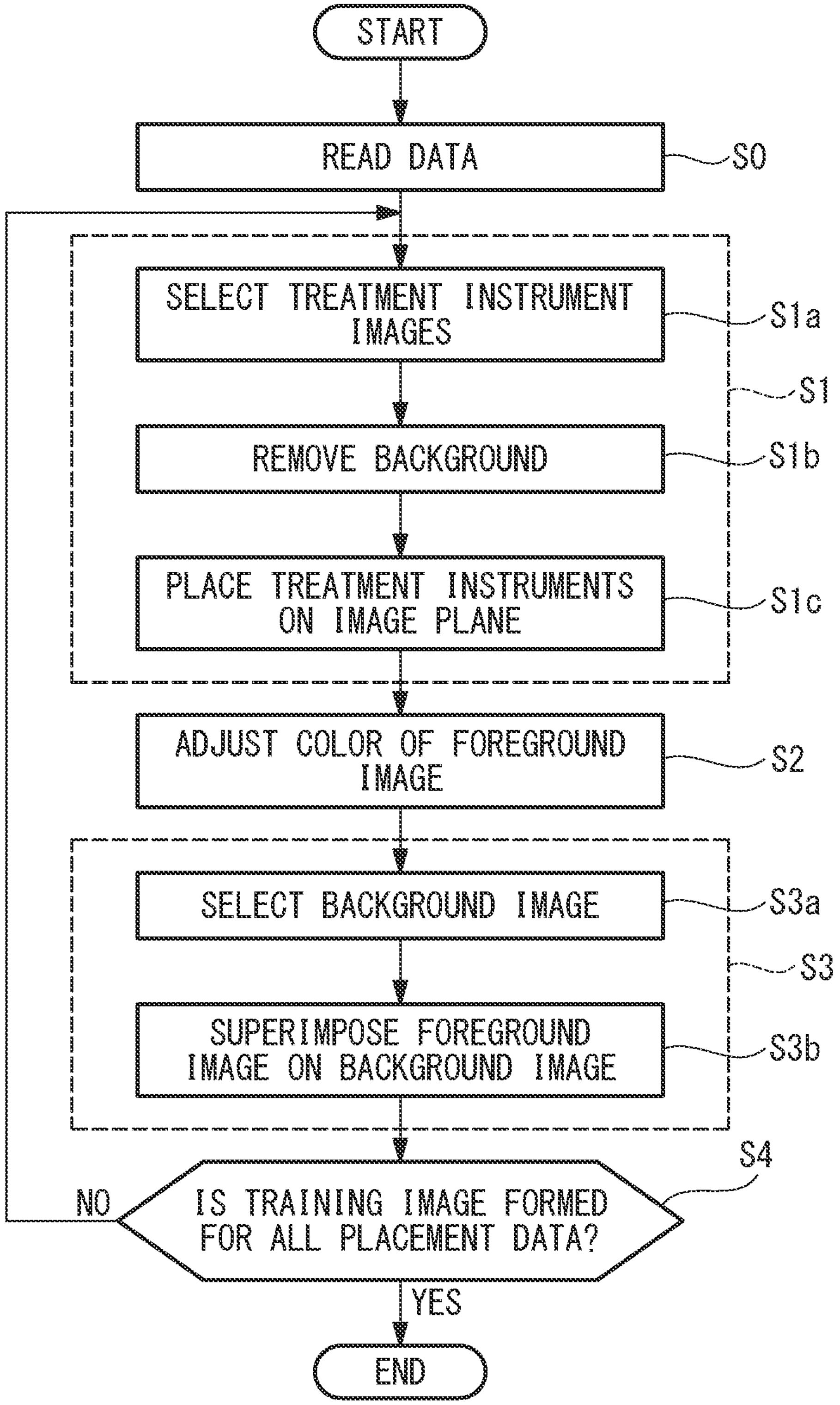
FIG. 7 is a flowchart of a method for supporting learning according to the first embodiment.

As shown in FIG. 7, the method for supporting learning according to the present embodiment includes step S1 of forming a foreground image C, step S2 of adjusting a color of the foreground image C, and step S3 of forming the training image D in which a foreground image C' with the adjusted color is superimposed on a background image.

Figure 8:
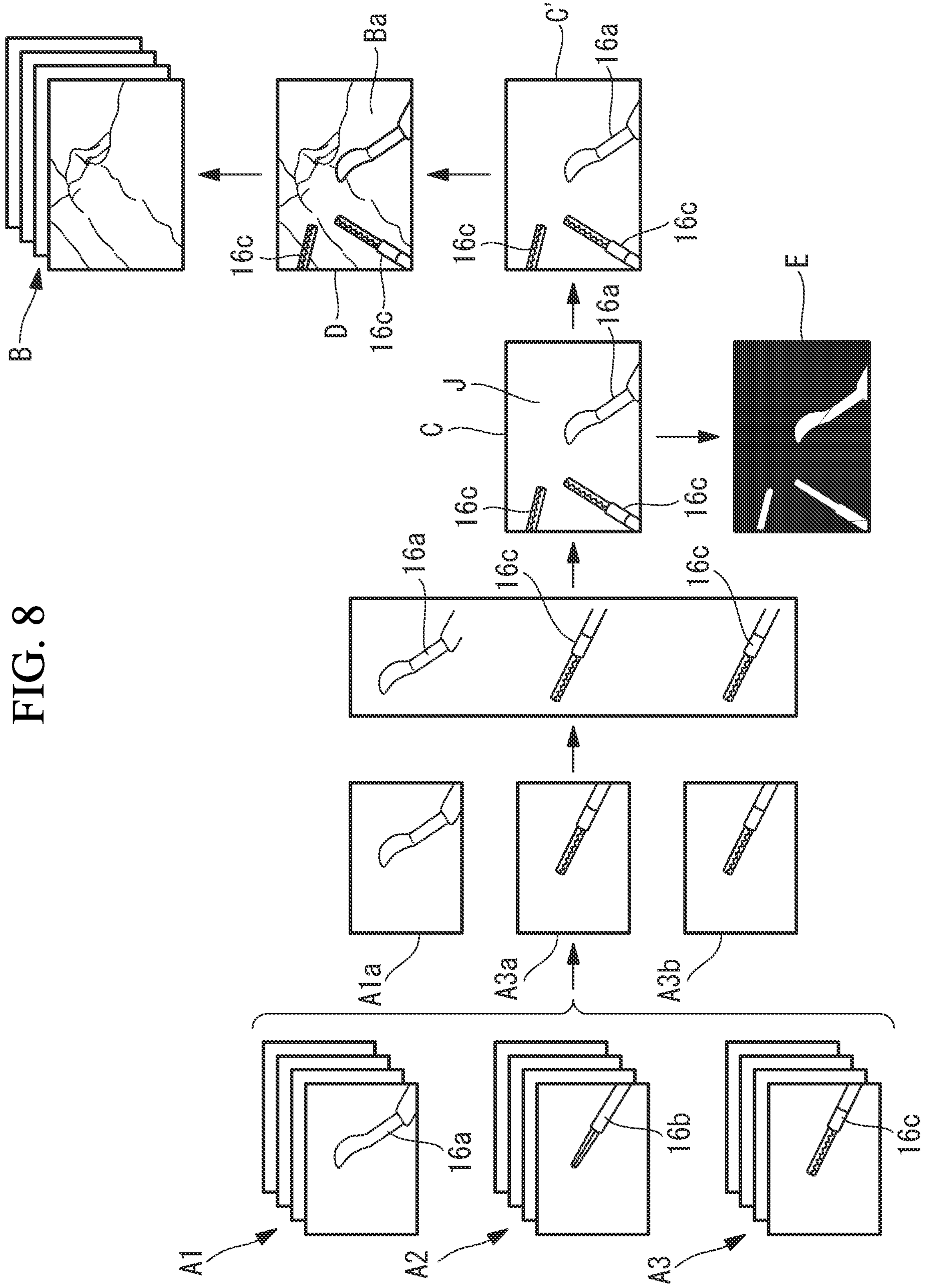
FIG. 8 is a diagram illustrating image processing in the method for supporting learning shown in FIG. 7.

FIG. 8 illustrates image processing in the method for supporting learning according to the present embodiment.

The processor 1 reads data necessary to perform the method for supporting learning, to be more specific, the image groups A1, A2, A3, . . . , B and the placement data 6*a*, from the storage unit 2 (step S0).

In step S1, from the plurality of treatment instrument image groups A1, A2, A3, . . . , the processor 1 forms the foreground image C containing at least one treatment instrument placed based on the placement data 6*a*.

To be more specific, from the treatment instrument image groups A1, A2, A3, . . . , the processor 1 selects at least one treatment instrument image, that is, treatment instrument images A1*a*, A3*a*, A3*b*, based on the placement data 6*a* (step S1*a*).

Figure 9:
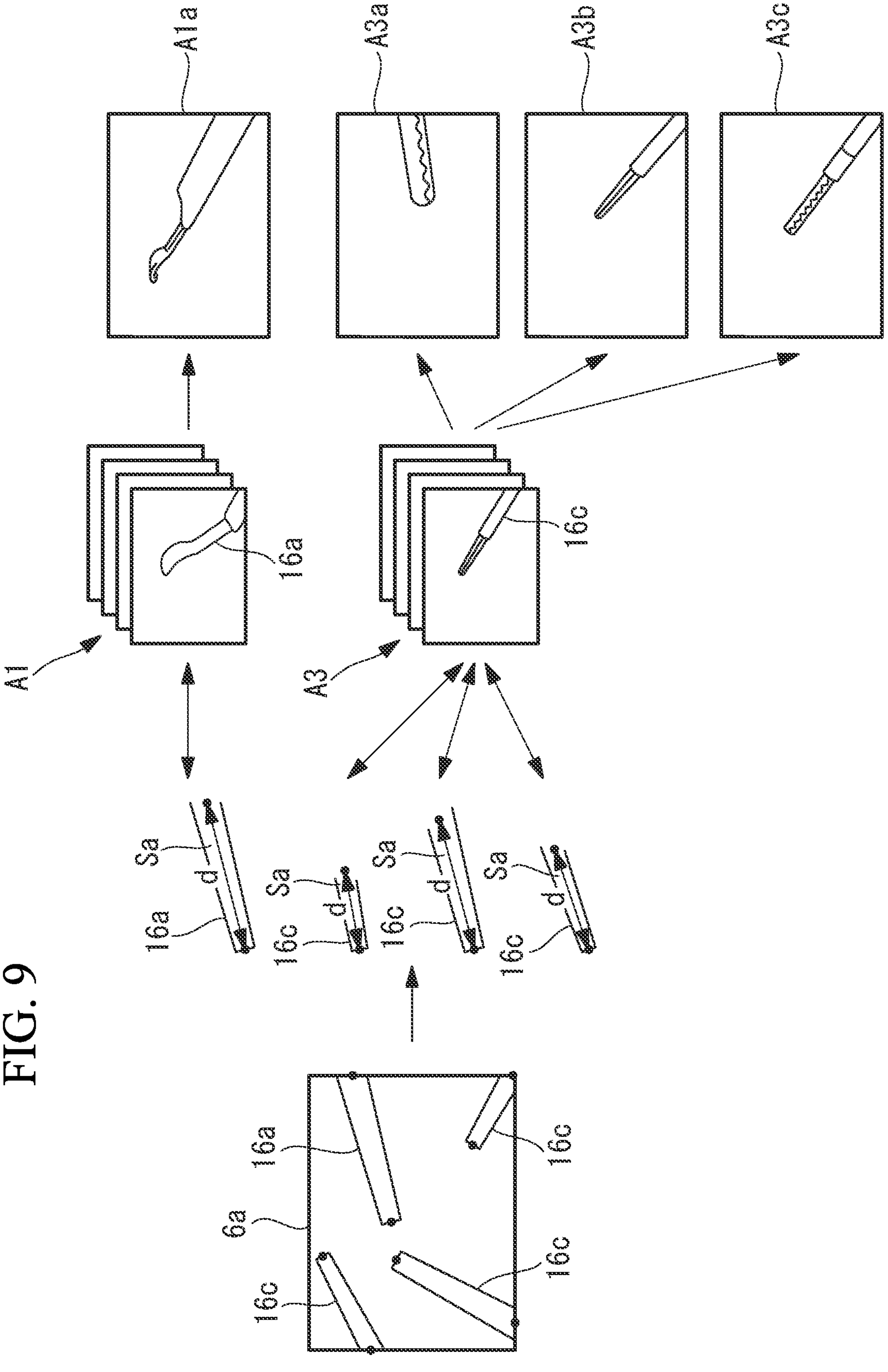
FIG. 9 is a diagram illustrating a method for selecting treatment instrument images based on the placement data.

FIG. 9 illustrates a method for selecting treatment instrument images based on a placement data 6*a* including one treatment instrument 16*a* and three treatment instruments 16*c*.

The processor 1 selects the image groups A1, A3 for the treatment instruments of the same kind as the treatment instruments included in the placement data 6*a* from the plurality of treatment instrument image groups A1, A2, A3, . . . . Next, the processor 1 calculates the length d of each treatment instrument from the placement data 6*a*, and selects treatment instrument images A1*a*, A3*a*, A3*b*, A3*c* of treatment instruments each having the same or close length and area as the length d and the area Sa, from the treatment instrument image groups A1, A3. For example, the processor 1 calculates coincidence of the length d and the area Sa with the length and the area of the treatment instrument within each treatment instrument image, and selects a treatment instrument image with coincidence being a threshold value or less.

Next, the processor 1 removes a background of each of the selected treatment instrument images A1*a*, A3*a*, A3*b* to extract an image of the treatment instrument 16*a*, 16*c* within the treatment instrument image A1*a*, A3*a*, A3*b* (step S1*b*).

Next, the processor 1 places the images of the treatment instruments 16*a*, 16*c* within a two-dimensional image region J based on the placement data 6*a*, thus forming the foreground image C (step S1*c*).

In the following step S2, the processor 1 adjusts the color of each of the treatment instruments 16*a*, 16*c* within the foreground image C based on distance information on each of the treatment instruments 16*a*, 16*c* included in the placement data 6*a*, thus forming the adjusted foreground image C'.

As used herein, "color" refers to saturation, hue, and brightness being three elements of color, and "adjust color" means to adjust at least one of saturation, hue, or brightness.

For example, the processor 1 estimates the distance from the endoscope to each of the treatment instruments 16*a*, 16*c* based on the length d and the area Sa of each of the treatment instruments 16*a*, 16*c*, and adjusts the brightness of each of the treatment instruments 16*a*, 16*c* such that the treatment instrument has a higher brightness at a portion thereof that is at a shorter distance.

The processor 1 may adjust saturation and hue based on the distance. For example, the processor 1 may adjust saturation such that the treatment instrument has higher saturation at a portion thereof that is at a shorter distance, and the processor 1 may adjust hue such that the treatment instrument has hue closer to the hue of illumination light of the endoscope (white, for example) at a portion thereof that is at a shorter distance.

In the following step S3, the processor 1 selects any one background image Ba from the background image group B (step S3*a*), and forms the training image D by superimposing the foreground image C' with the adjusted color on the background image Ba (step S3*b*).

The processor 1 repeats steps S1 to S3 to form a large number of training images D by using all placement data 6*a* (step S4). Thus, a large number of training images D are formed covering placement that may occur during endoscopic surgery with respect to the treatment instruments within the clinical image.

As described above, according to the present embodiment, the training image D is formed from the image groups A1, A2, A3, . . . , B, and a clinical image containing treatment instruments is not required. Accordingly, it is possible to form a training image D for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, the placement data 6*a* are created in advance based on the placement of treatment instruments during actual endoscopic surgery. By using such placement data 6*a*, it is possible to form a training image D with reality, that is, a training image D in which the placement and the colors of the treatment instruments are close to those in the clinical image. In addition to the above, by learning such a training image D, it is possible to form a learning model with high recognition accuracy for treatment instruments within the clinical image and hence, recognition performance for treatment instruments within an endoscopic image during endoscopic surgery can be enhanced.

To be more specific, the placement of treatment instruments within the foreground image C is determined based on the positions a, b, and the areas Sa, so that the placement of the treatment instruments within the training image D is the same as or close to the three-dimensional placement of the treatment instruments within the clinical image. Further, the color of each treatment instrument is adjusted based on the distance from the endoscope and hence, the color of each treatment instrument within the training image D becomes the same as or close to the color of each treatment instrument within the clinical image.

As described above, it is possible to form the training image D with small deviation from the clinical image with respect to the placement and the colors of the treatment instruments.

Figure 10:
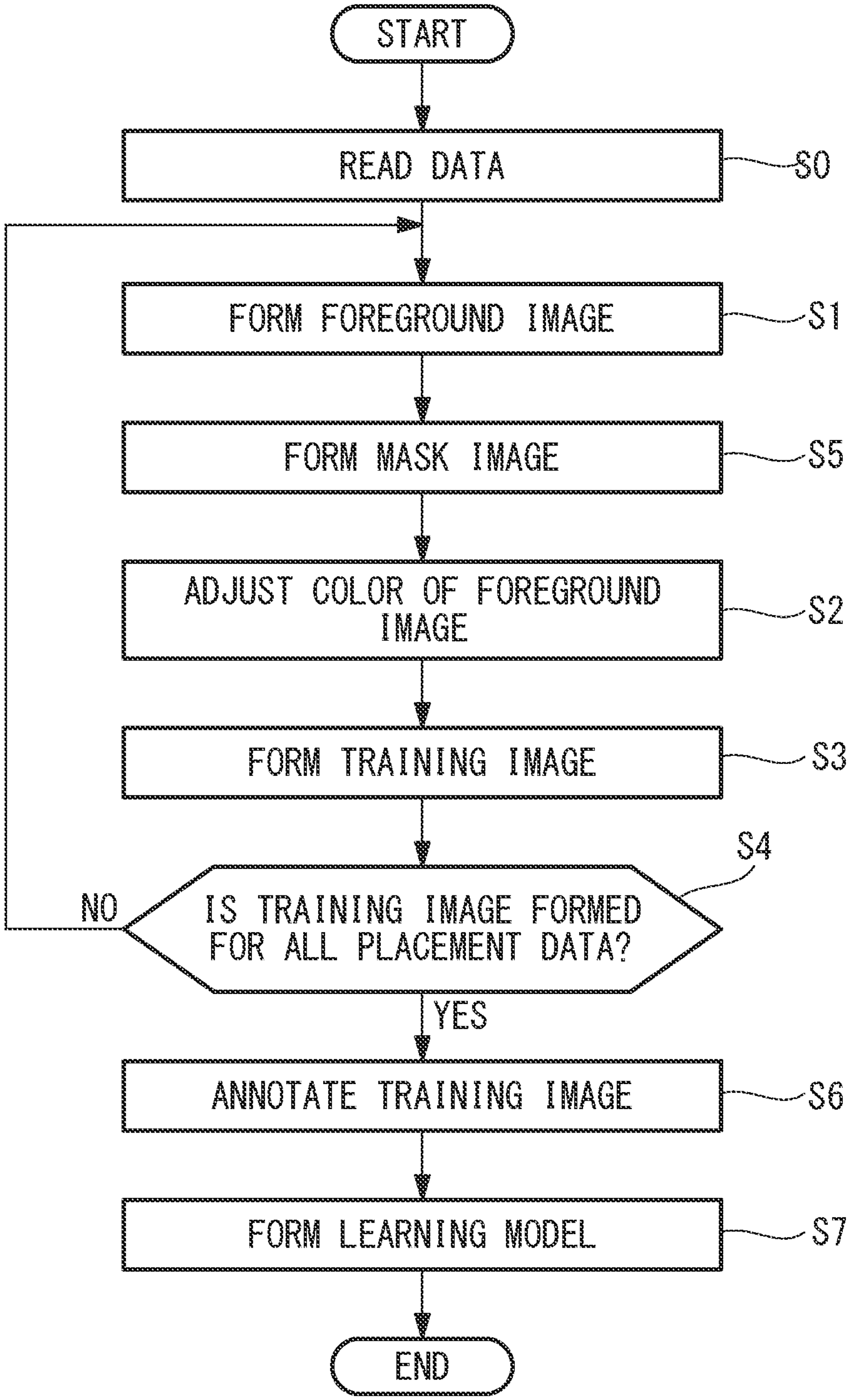
FIG. 10 is a flowchart of a modification of the method for supporting learning according to the first embodiment.

As shown in FIG. 10, the method for supporting learning of the present embodiment may further include step S5 of forming a mask image E based on the foreground image C, and step S6 of annotating the training image D based on the mask image E.

The timing of each of steps S5, S6 shown in FIG. 10 is merely an example, and may be suitably changed.

As shown in FIG. 8, the mask image E is an image obtained by extracting only the regions of the treatment instruments 16*a*, 16*c* within the foreground image C. In step S6, the processor 1 selects, from the training image D, regions at the same positions as the regions of the treatment instruments 16*a*, 16*c* within the mask image E, and labels the positions of the selected regions to the training image D as information on the positions of the regions of the treatment instruments.

To form a learning model that recognizes treatment instruments, it is necessary to perform annotation in which information on the positions of the regions of the treatment instruments is labeled to each training image D. By automatically annotating the training image D by forming the mask image E from the foreground image C, it is possible to cause the processor 1 to perform annotation of a large number of training images D. Further, the positions of the regions of the treatment instruments within the foreground image C coincide with the positions of the regions of the treatment instruments within the training image D and hence, by using the mask image E formed from the foreground image C, it is possible to accurately annotate the training image D.

As shown in FIG. 10, the method for supporting learning of the present embodiment may further include step S7 of learning a plurality of training images D to form a learning model that recognizes treatment instruments within the endoscopic image. In this case, the storage unit 2 further stores a learning-use model 7 that forms a learning model by learning the training image D (see FIG. 3).

After performing annotation, the processor 1 causes the learning-use model 7 to learn a large number of annotated training images D, thus causing the learning-use model 7 to form a learning model.

Such a configuration allows the learning support device 10 to perform the whole process from formation of a training image D to formation of a learning model.

The method for supporting learning of the present embodiment may not include step S2. That is, in step S3, the processor 1 may form the training image D by superimposing the foreground image C on the background image Ba.

The foreground image C formed based on the placement data 6*a* is an image in which the placement of treatment instruments is close to that in the clinical image. Accordingly, by using the foreground image C, it is also possible to form a training image D with reality.

Second Embodiment

Next, a learning support device and a method for supporting learning according to a second embodiment of the present invention will be described.

The present embodiment differs from the first embodiment with respect to a point that a foreground image C is formed from CG (computer graphics) instead of treatment instrument images. In the present embodiment, components that are different from the components in the first embodiment will be described. Components identical to the corresponding components in the first embodiment are given the same reference symbols, and the description of such components will be omitted.

Figure 11:
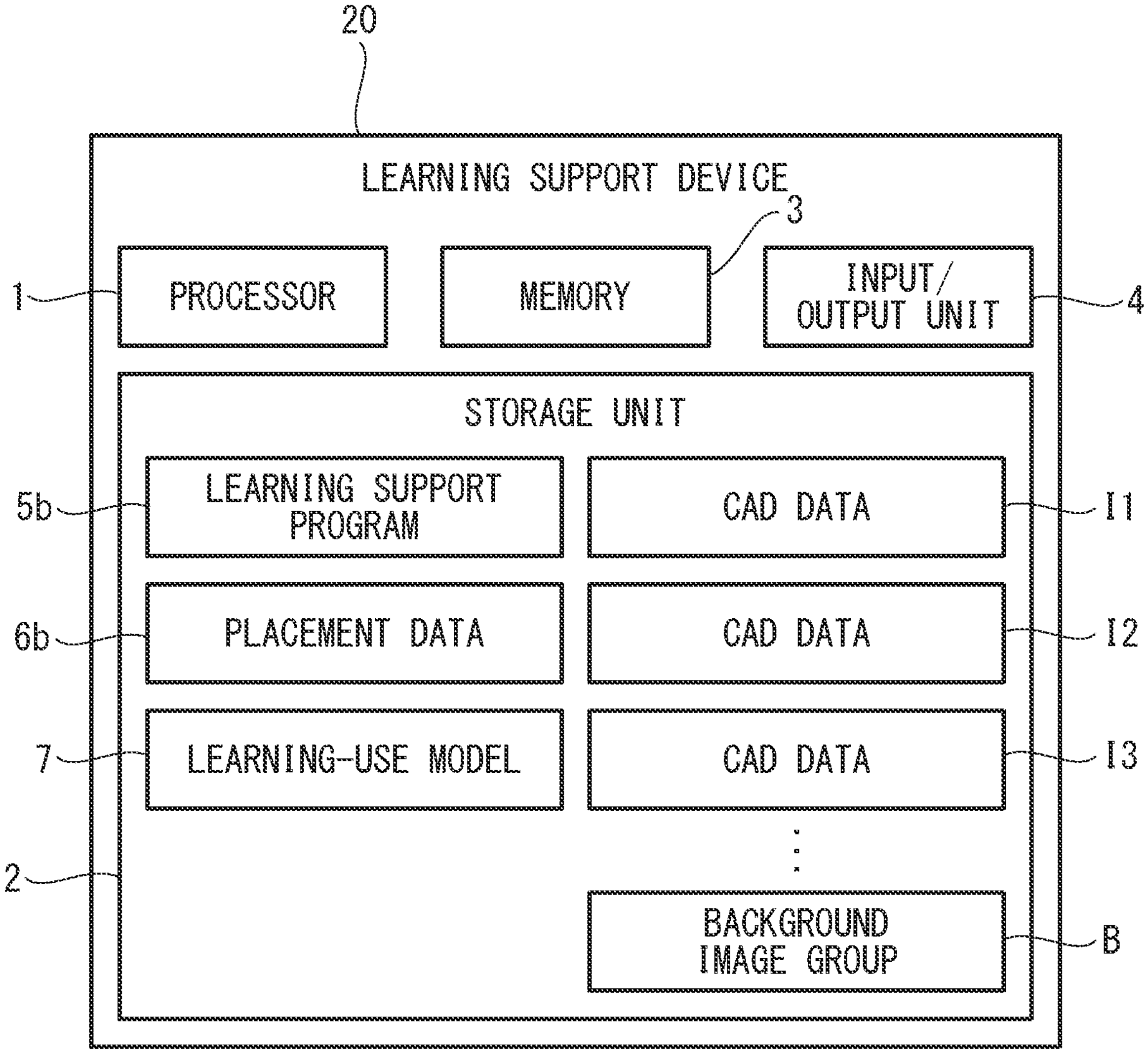
FIG. 11 is a block diagram showing a configuration of a learning support device according to a second embodiment.

As shown in FIG. 11, a learning support device 20 according to the present embodiment includes a processor 1, a storage unit 2, a memory 3, and an input/output unit 4.

The storage unit 2 stores a learning support program 5*b* that causes the processor 1 to perform the method for supporting learning according to the present embodiment, which will be described later. The storage unit 2 further stores a plurality of CAD (computer aided design) data I1, I2, I3, . . . , a background image group B, and placement data 6*b*, all of which are necessary for the method for supporting learning.

The CAD data I1, I2, I3, . . . are respectively three-dimensional CAD data of three-dimensional models of treatment instruments 16*a*, 16*b*, 16*c*, . . . , and the treatment instruments 16*a*, 16*b*, 16*c*, . . . differ from each other.

The placement data 6*b* includes information on the number of treatment instruments, and the position and the orientation of each treatment instrument. The position and the orientation of a treatment instrument are the three-dimensional position and orientation of the treatment instrument as viewed through an endoscope. In the present embodiment, distance information includes information on position and orientation.

Also in the present embodiment, a large number of sets of placement data 6*b* are prepared covering all placements that may occur during endoscopic surgery with respect to treatment instruments within the clinical image. For example, thousands of sets of placement data 6*b* or more are prepared.

Figure 12:
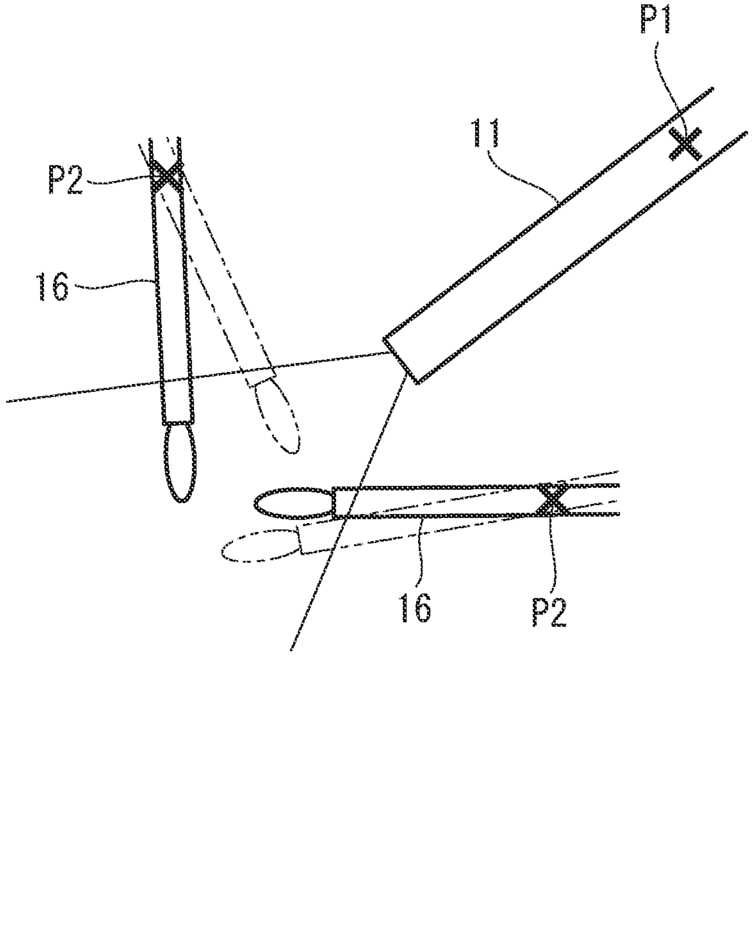
FIG. 12 is a diagram illustrating a method for creating placement data.

FIG. 12 illustrates an example of a method for creating the placement data 6*b*.

As described above, the three-dimensional position and orientation that each of the treatment instruments 16 may take with respect to the distal end of the endoscope 11 is limited within a certain range determined by the placement of the ports P1, P2 and the observation range Q for each surgical method. By comprehensively changing the position and the orientation of each of the treatment instruments 16 with respect to the distal end of the endoscope 11 within the above-mentioned certain range, a large number of sets of placement data 6*b* are created covering the number of treatment instruments within the clinical image, and the position and the orientation of each treatment instrument within the clinical image.

Next, the method for supporting learning that is performed by the learning support device 20 will be described.

Figure 13:
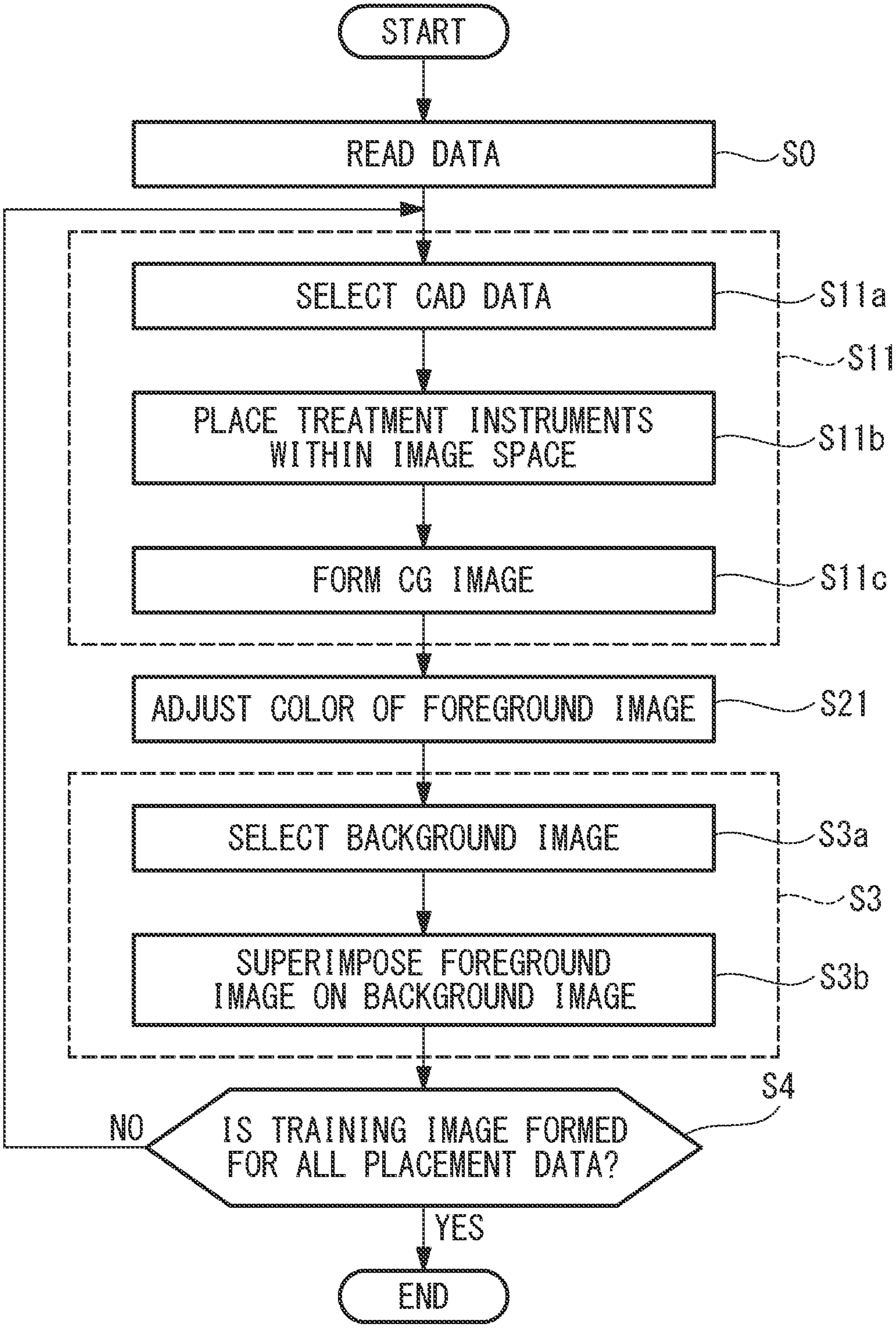
FIG. 13 is a flowchart of a method for supporting learning according to the second embodiment.

As shown in FIG. 13, the method for supporting learning according to the present embodiment includes step S11 of forming a foreground image C, step S21 of adjusting the color of the foreground image C, and step S3 of forming a training image D in which a foreground image C' with the adjusted color is superimposed on a background image.

Figure 14:
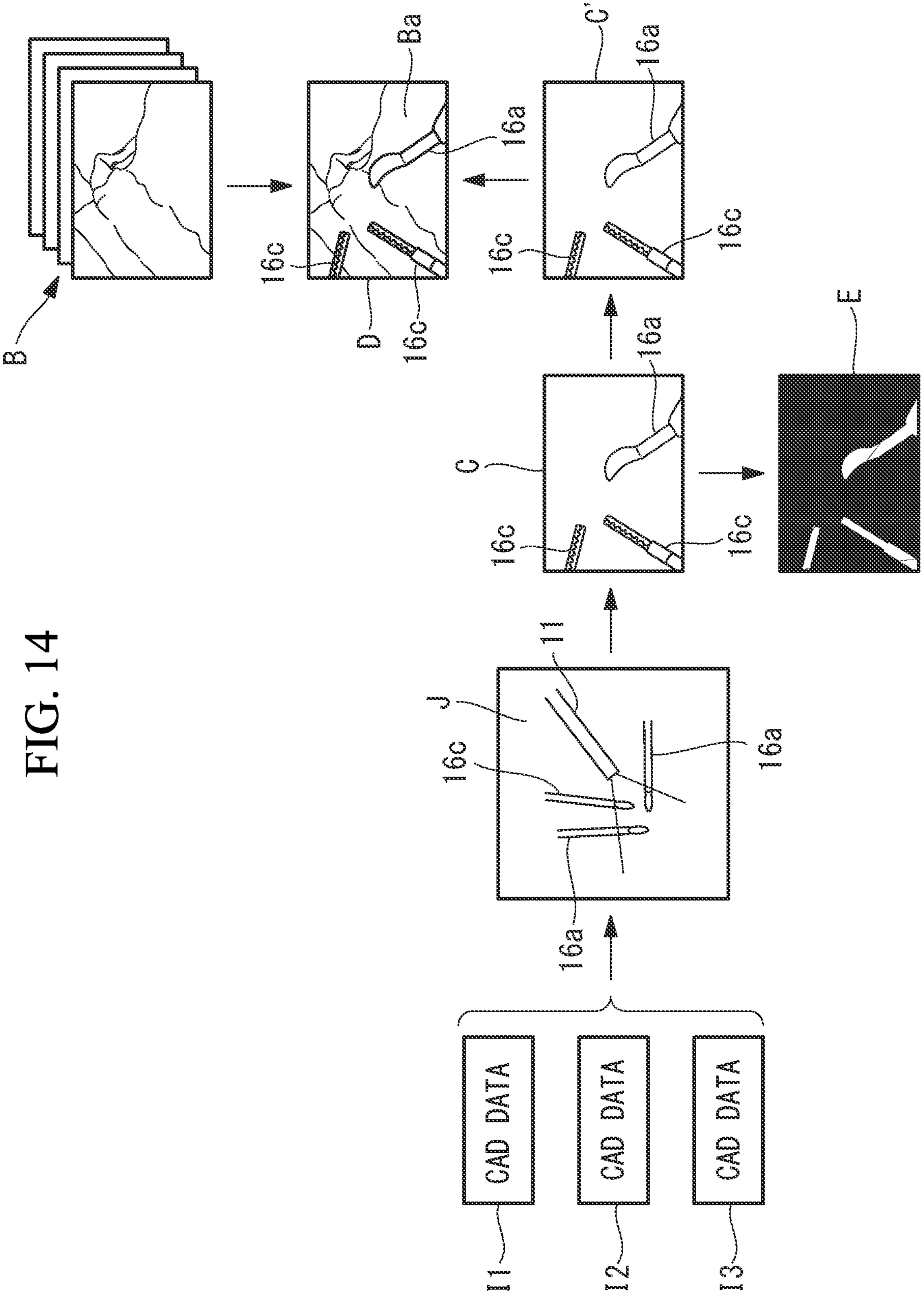
FIG. 14 is a diagram illustrating image processing in the method for supporting learning shown in FIG. 13.

FIG. 14 illustrates image processing in the method for supporting learning according to the present embodiment.

The processor 1 reads data necessary to perform the method for supporting learning, to be more specific, the CAD data I1, I2, I3, . . . , the background image group B, and the placement data 6*b*, from the storage unit 2 (step S0).

In step S11, from the plurality of sets of CAD data I1, I2, I3, . . . , the processor 1 forms the foreground image C containing at least one treatment instrument placed based on the placement data 6*b*.

To be more specific, from the plurality of sets of CAD data I1, I2, I3, . . . , the processor 1 selects CAD data of treatment instruments of the same kind as the treatment instruments included in the placement data 6*b* (step S11*a*).

Next, based on the position and the orientation of each treatment instrument in the placement data 6*b*, the processor 1 places images of the treatment instruments 16*a*, 16*c* within a three-dimensional image region J, thus forming three-dimensional CG images, the images of the treatment instruments 16*a*, 16*c* being three-dimensional models formed from CAD data (step S11*b*).

Next, the processor 1 converts the three-dimensional CG image to two dimensions based on the position and the orientation of the treatment instruments 16*a*, 16*c* as viewed through the endoscope 11, thus forming the foreground image C being a two-dimensional CG image of the treatment instruments 16*a*, 16*c* as viewed through the endoscope (step S11*c*).

In the following step S21, the processor 1 adjusts the color of each of the treatment instruments 16*a*, 16*c* within the foreground image C based on distance information on each treatment instrument included in the placement data 6*b*, thus forming the foreground image C'.

For example, the processor 1 calculates the distance from the endoscope to each of the treatment instruments 16*a*, 16*c* from the position and the orientation of each of the treatment instruments 16*a*, 16*c*, and adjusts the brightness of each of the treatment instruments 16*a*, 16*c* such that the treatment instrument has a higher brightness at a portion thereof that is at a shorter distance. In the same manner as the first embodiment, the processor 1 may adjust saturation and hue based on the distance.

Steps S3, S4 are as described in the first embodiment.

As described above, according to the present embodiment, the training image D is formed from CAD data 11, 12, 13, and the background image group B, and a clinical image containing treatment instruments is not required. Accordingly, it is possible to form a training image D for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, the placement data 6*b* are created in advance based on the placement of treatment instruments during actual endoscopic surgery. By using such placement data 6*b*, it is possible to form a training image D with reality, that is, a training image D in which the placement and the colors of the treatment instruments are close to those in the clinical image. In addition to the above, by learning such a training image D, it is possible to form a learning model with high recognition accuracy for treatment instruments within the clinical image and hence, recognition performance for treatment instruments within an endoscopic image during endoscopic surgery can be enhanced.

To be more specific, the placement of the treatment instruments within the foreground image C is determined based on the position and the orientation of each treatment instrument included in the placement data 6*b*, so that the placement of the treatment instruments within the training image D is the same as or close to the three-dimensional placement of the treatment instruments within the clinical image. Further, the color of each treatment instrument is adjusted based on the distance from the endoscope and hence, the color of each treatment instrument within the training image D becomes the same as or close to the color of each treatment instrument within the clinical image.

As described above, it is possible to form a training image D with small deviation from the clinical image with respect to the placement and the colors of the treatment instruments.

In the same manner as the first embodiment, the method for supporting learning of the present embodiment may further include steps S5, S6, S7, and may not include step S2.

Third Embodiment

Next, a learning support device and a method for supporting learning according to a third embodiment of the present invention will be described.

The present embodiment differs from the first embodiment with respect to a point that the color of a foreground image C is adjusted based on illumination of an endoscope 11. In the present embodiment, components that are different from the components in the first embodiment will be described. Components identical to the corresponding components in the first embodiment are given the same reference symbols, and the description of such components will be omitted.

Figure 15:
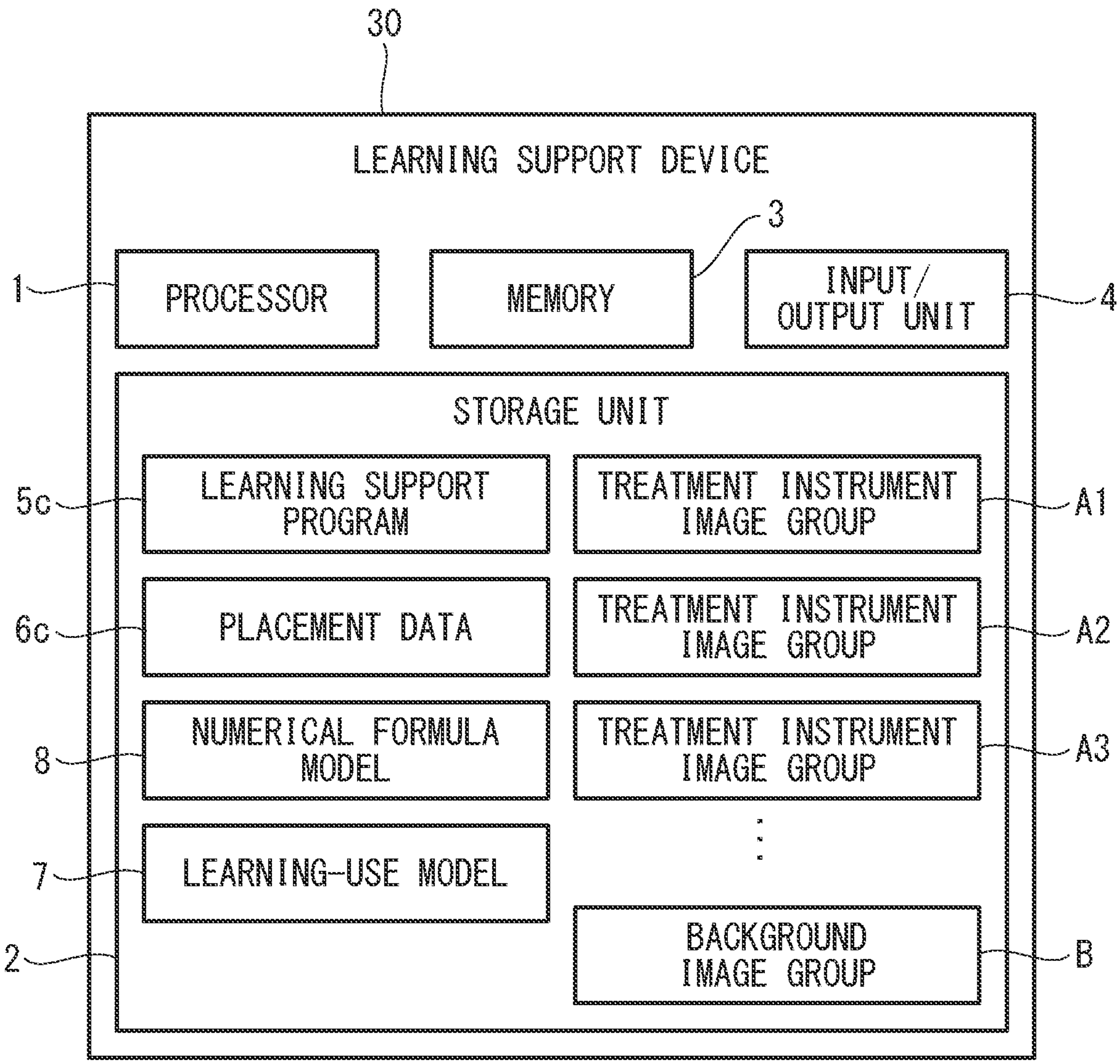
FIG. 15 is a block diagram showing a configuration of a learning support device according to a third embodiment.

As shown in FIG. 15, a learning support device 30 according to the present embodiment includes a processor 1, a storage unit 2, a memory 3, and an input/output unit 4.

The storage unit 2 stores a learning support program 5*c* that causes the processor 1 to perform the method for supporting learning according to the present embodiment, which will be described later. The storage unit 2 further stores sample image groups A1, A2, A3, . . . , B, placement data 6*c*, and a numerical formula model 8 for illumination, all of which are necessary for the method for supporting learning.

The placement data 6*c* include information on the position and the orientation of each treatment instrument as viewed through an endoscope in addition to information on the number of treatment instruments, the kind of each treatment instrument, the positions of the distal end and the proximal end of each treatment instrument, and the area of each treatment instrument, which are described in the first embodiment.

Information on position and orientation is information on the three-dimensional position and the orientation of the treatment instrument as viewed through the endoscope. For example, information on position and orientation is information on the three-dimensional position and orientation of a treatment instrument with respect to the endoscope when a treatment instrument image is photographed by the endoscope, and the treatment instrument image and the information on position and orientation are stored as a pair in the storage unit 2. In the present embodiment, distance information includes information on position and orientation.

Figure 16:
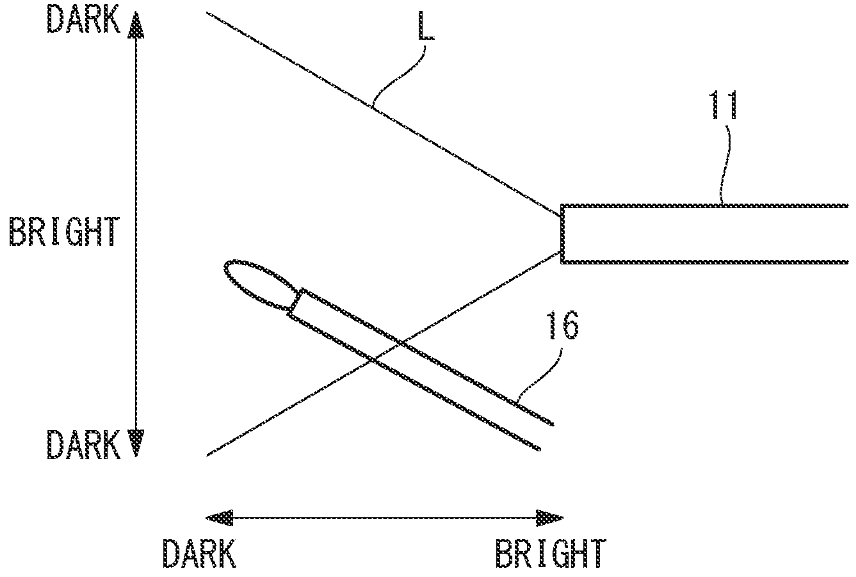
FIG. 16 is a diagram illustrating a spatial distribution of luminance of illumination light of an endoscope.

As shown in FIG. 16, during endoscopic surgery, a treatment instrument 16 is illuminated by illumination light L emitted from the distal end of the endoscope 11. The illumination light L has a spatial distribution of luminance, and becomes darker as the illumination light L increases in distance from the distal end of the endoscope 11. Accordingly, the brightness of the treatment instrument within the clinical image decreases more as the treatment instrument increases in distance from the distal end of the endoscope 11.

The numerical formula model 8 is a numerical formula model expressing a spatial distribution of the luminance of the illumination light L, and is formed based on the endoscope 11 used in endoscopic surgery and optical properties of the illumination light L, for example.

Next, the method for supporting learning that is performed by the learning support device 30 will be described.

Figure 17:
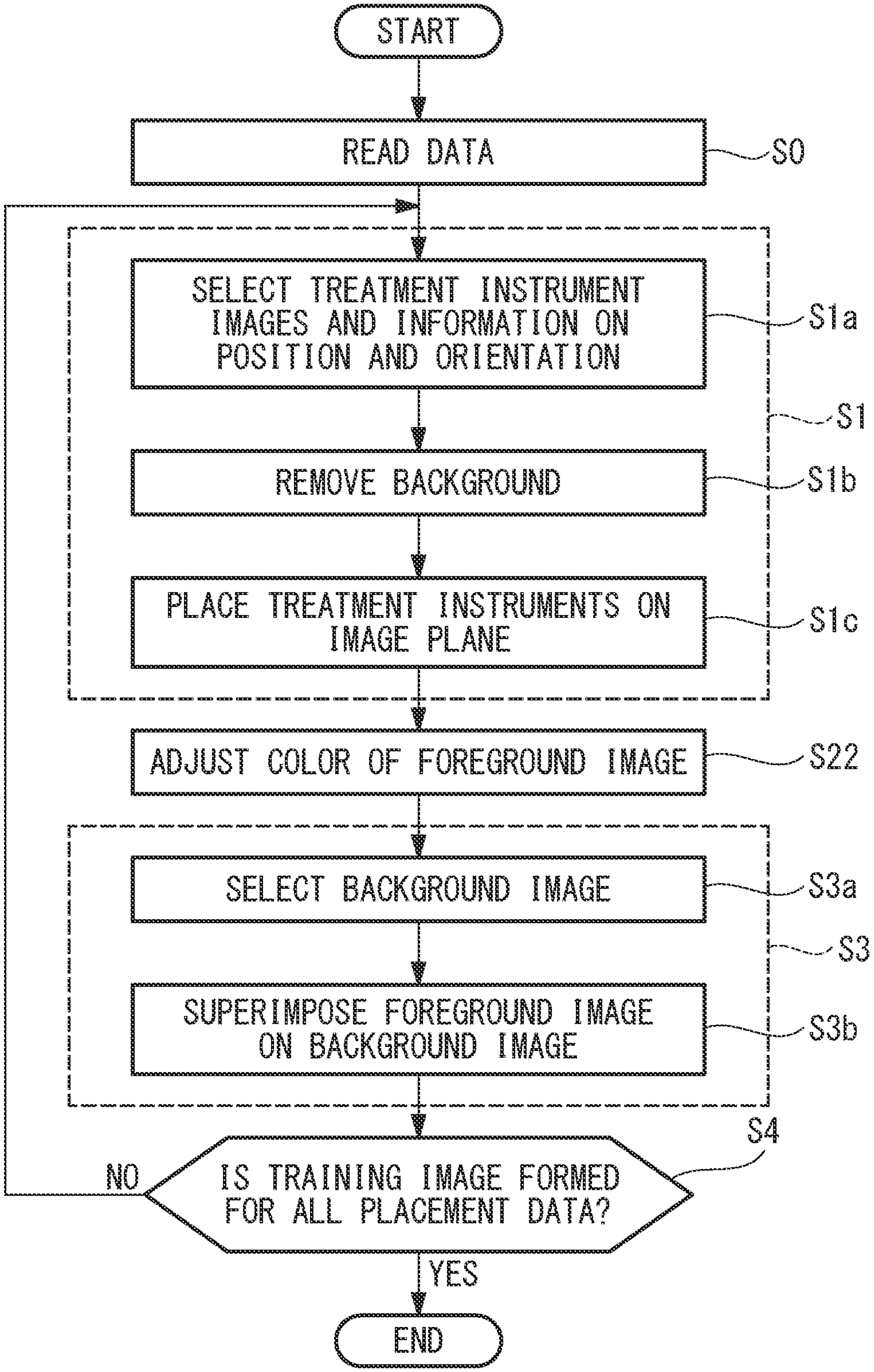
FIG. 17 is a flowchart of a method for supporting learning according to the third embodiment.

As shown in FIG. 17, the method for supporting learning according to the present embodiment includes step S1 of forming a foreground image C, step S22 of adjusting the color of the foreground image C, and step S3 of forming a training image D in which a foreground image C' with the adjusted color is superimposed on a background image.

The processor 1 reads data necessary to perform the method for supporting learning, to be more specific, the image groups A1, A2, A3, . . . , B, the placement data 6*c*, and the numerical formula model 8, from the storage unit 2 (step S0).

In step S1, the processor 1 selects at least one treatment instrument image, that is, treatment instrument images A1*a*, A3*a*, A3*b*, from the treatment instrument image groups A1, A2, A3, . . . together with information on position and orientation (step S1*a*). Other processes in step S1 are as described in the first embodiment.

In step S22, the processor 1 adjusts the brightness of each treatment instrument within the foreground image C based on information on position and orientation of each treatment instrument within the foreground image C and based on the numerical formula model 8, thus forming the foreground image C'. In the foreground image C', the brightness of each treatment instrument varies depending on the distance from the endoscope 11, and the treatment instrument has a higher brightness at a portion thereof that is at a shorter distance.

Steps S3, S4 are as described in the first embodiment.

In the same manner as the first embodiment, according to the present embodiment, it is possible to form a training image D for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, the placement data 6*c* are used and hence, it is possible to form a training image D with reality, that is, a training image D in which the placement of the treatment instruments is close to that in the clinical image. Accordingly, it is possible to form a learning model with high recognition accuracy for treatment instruments within the clinical image and hence, recognition performance for treatment instruments within an endoscopic image during endoscopic surgery can be enhanced.

Further, according to the present embodiment, the brightness of each treatment instrument within the foreground image C is adjusted based on information on position and orientation and the numerical formula model 8, so that the brightness of each treatment instrument within the training image D becomes the same as or close to the brightness of each treatment instrument within the clinical image. The training image D with small deviation from the clinical image with respect to the brightness of treatment instruments can be formed from such a foreground image C'.

In the same manner as the first embodiment, the method for supporting learning of the present embodiment may also further include steps S5, S6, S7.

In the present embodiment, the processor 1 may form a foreground image C from CG (computer graphics) instead of treatment instrument images.

That is, the storage unit 2 may store the CAD data I1, I2, I3, . . . described in the second embodiment instead of the treatment instrument image groups A1, A2, A3, . . . , and the method for supporting learning of the present embodiment may include step S11 described in the second embodiment instead of step S1.

Fourth Embodiment

Next, a learning support device and a method for supporting learning according to a fourth embodiment of the present invention will be described.

The present embodiment differs from the first embodiment with respect to a point that the color of a foreground image C is adjusted based on a brightness distribution of a background image in addition to a distance from an endoscope. In the present embodiment, components that are different from the components in the first embodiment will be described. Components identical to the corresponding components in the first embodiment are given the same reference symbols, and the description of such components will be omitted.

Figure 18:
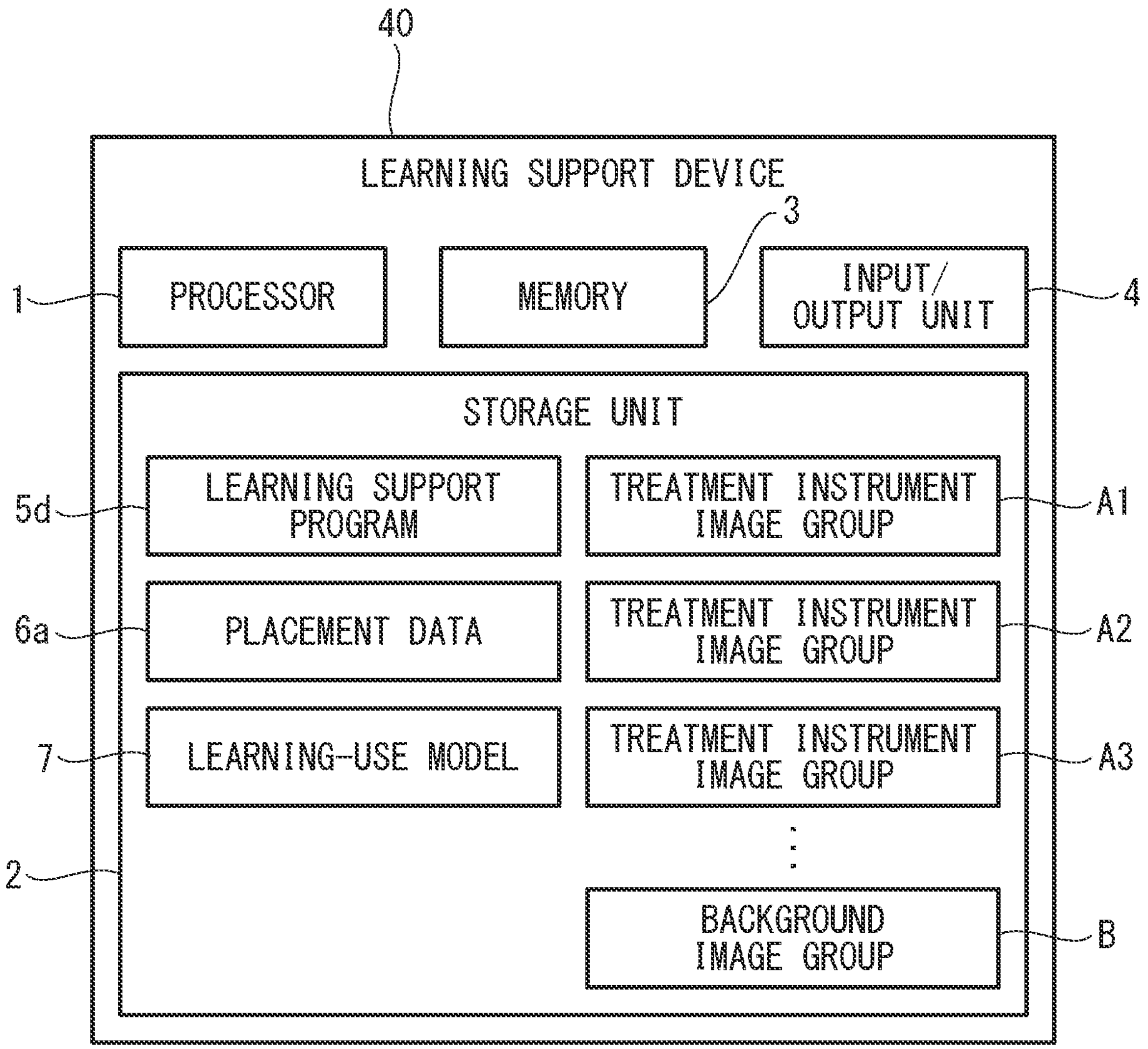
FIG. 18 is a block diagram showing a configuration of a learning support device according to a fourth embodiment.

As shown in FIG. 18, a learning support device 40 according to the present embodiment includes a processor 1, a storage unit 2, a memory 3, and an input/output unit 4.

The storage unit 2 stores a learning support program 5*d* that causes the processor 1 to perform the method for supporting learning according to the present embodiment, which will be described later. The storage unit 2 further stores sample image groups A1, A2, A3, . . . , B, and placement data 6*a*, all of which are necessary for the method for supporting learning.

Next, the method for supporting learning that is performed by the learning support device 40 will be described.

Figure 19:
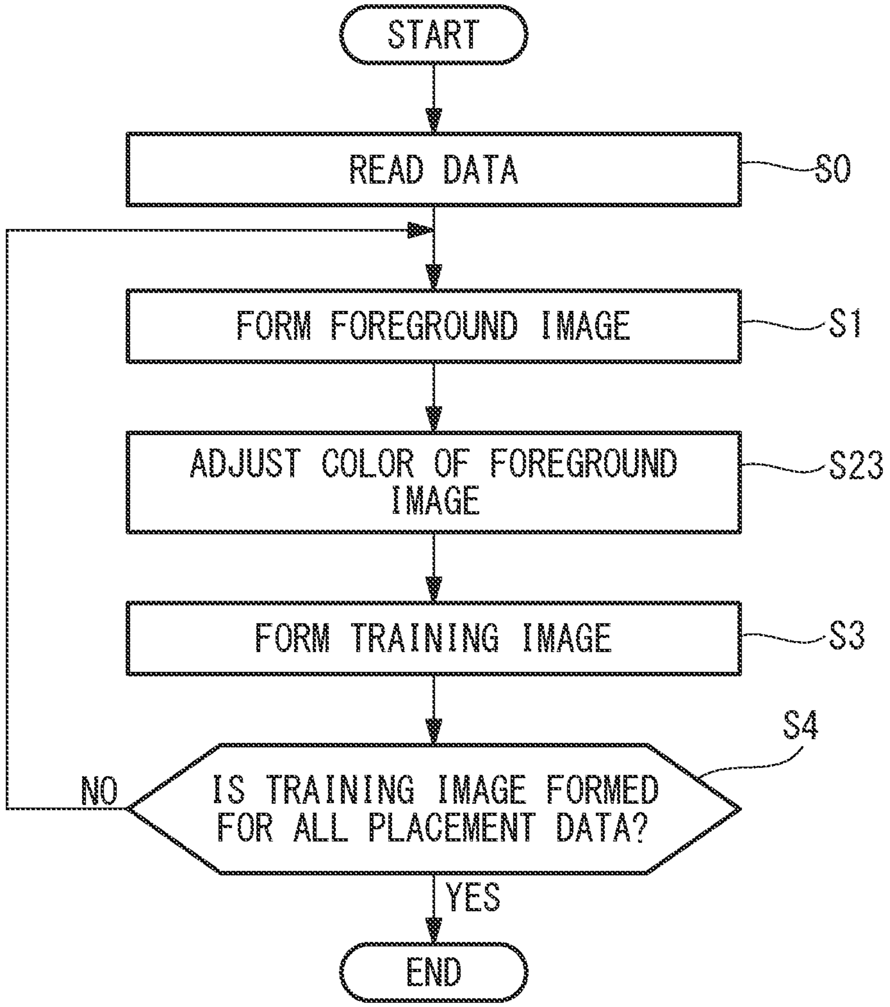
FIG. 19 is a flowchart of a method for supporting learning according to the fourth embodiment.

As shown in FIG. 19, the method for supporting learning according to the present embodiment includes step S1 of forming a foreground image C, step S23 of adjusting the color of the foreground image C, and step S3 of forming a training image D in which a foreground image C' with the adjusted color is superimposed on a background image.

Steps S0, S1, S4 are as described in the first embodiment.

In step S23, the processor 1 selects one background image Ba from the background image group B, and adjusts the brightness of each treatment instrument within the foreground image C based on the distance from the endoscope to each treatment instrument and based on a brightness distribution of the background image Ba.

Figure 20:
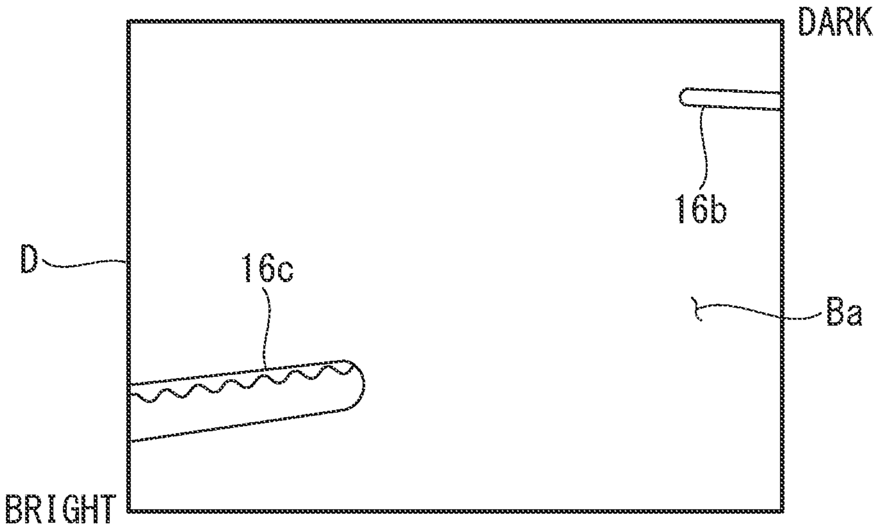
FIG. 20 is a diagram illustrating adjustment of brightness of treatment instruments based on a brightness distribution of a background image.

FIG. 20 shows an example of the training image D.

To be more specific, the processor 1 selects treatment instruments having a distance of a predetermined value or more from at least one treatment instrument within the foreground image C. The processor 1 performs the following adjustment of brightness on the selected treatment instruments, but does not perform adjustment of brightness on treatment instruments having a distance of less than the predetermined value, thus not being selected.

As will be described later, brightness is adjusted according to the brightness of a background. When a treatment instrument is disposed at a short distance, the brightness of the treatment instrument is more likely to be affected by illumination light from the endoscope than the brightness of the background, and when a treatment instrument is disposed at a greater distance, the brightness of the treatment instrument is dominantly affected by the brightness of the background more than by illumination light. Accordingly, adjustment of brightness is selectively performed on treatment instruments for which a distance is a predetermined value or more.

Next, the processor 1 adjusts brightness of the treatment instruments 16*b*, 16*c* according to the brightness of the background image Ba in a region on which the selected treatment instruments 16*b*, 16*c* are superimposed such that the brightness of the treatment instrument is increased for a background image Ba having a higher brightness. For example, as shown in FIG. 20, in the case in which the background image Ba has a brightness distribution in which the left lower portion is bright and the right upper portion is dark, the brightness of the treatment instrument 16*c* at the left lower portion is adjusted to a high brightness, and the brightness of the treatment instrument 16*b* at the right upper portion is adjusted to a low brightness.

In the following step S3, the processor 1 forms the training image D by superimposing the foreground image C' on the background image Ba selected in step S22.

In an example, the processor 1 adjusts brightness according to the following formula (1), thus adjusting the brightness of the region of the treatment instrument according to a difference from the average brightness of the background image.

$$(b, g, r) = (b + \mathrm{br\_shift}, g + \mathrm{br\_shift}, r + \mathrm{br\_shift})$$

In this formula, (b, g, r) is an RGB value of each pixel of the region of the treatment instrument within the foreground image C, "br" denotes the brightness of each pixel of the background image, "Br" denotes the average brightness of the background image, and br_shift=br−Br.

In the same manner as the first embodiment, according to the present embodiment, it is possible to form a training image D for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, by using the placement data 6*a*, it is possible to form a training image D with reality, that is, a training image D in which the placement of the treatment instruments is close to that in the clinical image. Accordingly, it is possible to form a learning model with high recognition accuracy for treatment instruments within the clinical image and hence, recognition performance for treatment instruments within an endoscopic image during endoscopic surgery can be enhanced.

Further, according to the present embodiment, the brightness of each treatment instrument within the foreground image C is adjusted based on a brightness distribution of the background image, thus allowing the brightness of each treatment instrument within the training image D to be the same or close to the brightness of each treatment instrument within the clinical image. The training image D with small deviation from the clinical image with respect to the brightness of treatment instruments can be formed from such a foreground image C'.

In the same manner as the first embodiment, the method for supporting learning of the present embodiment may also further include steps S5, S6, S7.

In the present embodiment, the processor 1 may form a foreground image C from CG (computer graphics) instead of treatment instrument images.

That is, the storage unit 2 may store the CAD data I1, I2, I3, . . . described in the second embodiment instead of the treatment instrument image groups A1, A2, A3, . . . , and the method for supporting learning of the present embodiment may include step S11 described in the second embodiment instead of step S1.

Fifth Embodiment

Next, a learning support device and an endoscope system according to a fifth embodiment of the present invention will be described.

Figure 21:
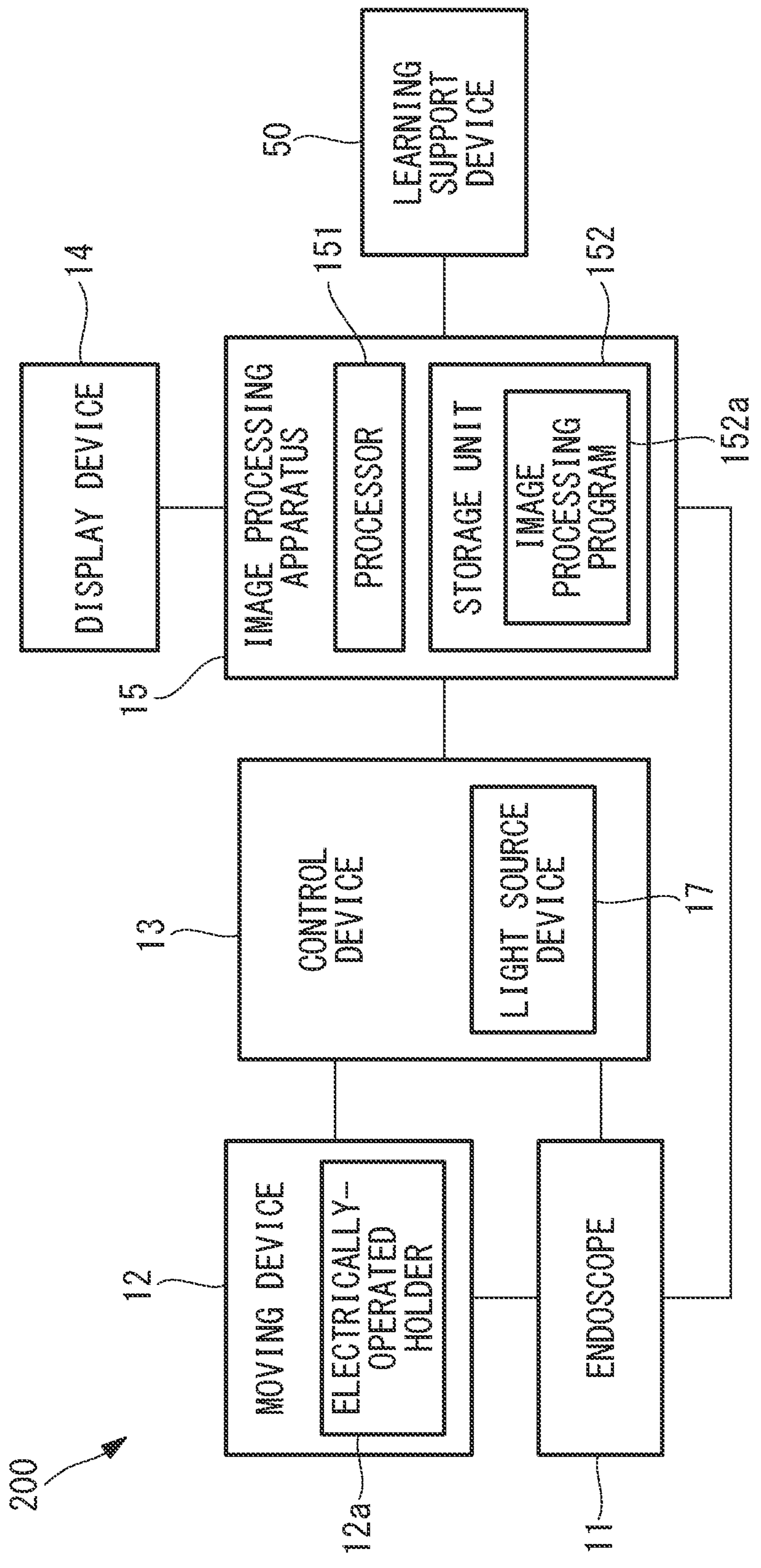
FIG. 21 is a block diagram showing a configuration of an endoscope system according to a fifth embodiment.

As shown in FIG. 21, an endoscope system 200 according to the present embodiment includes an endoscope 11, a moving device 12 that changes the position and the orientation of the endoscope 11, a control device 13 that controls the endoscope 11 and the moving device 12, a display device 14, an image processing apparatus 15, and a learning support device 50.

In the same manner as the endoscope system 100 described in the first embodiment, the endoscope system 200 is used for laparoscopic surgery, for example.

The endoscope 11 includes a camera including an imaging element, such as a CCD image sensor or a CMOS image sensor, and acquires an endoscopic image G in a subject X by the camera. The camera may be a three-dimensional camera that acquires stereo images.

The endoscopic image G is transmitted to the display device 14 via the control device 13 or the image processing apparatus 15 from the endoscope 11, and is displayed on the display device 14. The display device 14 is an arbitrary display, such as a liquid crystal display or an organic EL display.

The moving device 12 includes an electrically-operated holder 12*a* formed of an articulated robot arm, and is controlled by the control device 13. The endoscope 11 is held at a distal end portion of the electrically-operated holder 12*a*, and the position and orientation of the distal end of the endoscope 11 are three-dimensionally changed by the action of the electrically-operated holder 12*a*. The moving device 12 may be another mechanism that can change the position and orientation of the distal end of the endoscope 11, such as a bending portion provided at the distal end portion of the endoscope 11.

The control device 13 includes a processor, a storage unit, a memory, an input/output interface, and the like. The control device 13 also includes a light source device 17 connected to the endoscope 11, thus being capable of controlling intensity of illumination light L supplied from the light source device 17 to the endoscope 11. The light source device 17 may be separated from the control device 13.

As described in the first embodiment, the control device 13 performs tracking control that causes the field of view of the endoscope 11 to track a predetermined treatment instrument 16 as the target to be tracked. For example, in the tracking control, the control device 13 obtains the three-dimensional position of the distal end of the treatment instrument 16 from a stereo endoscopic image G, and controls the moving device 12 based on the position of the distal end.

The image processing apparatus 15 includes a processor 151, a storage unit 152, a memory, an input/output unit, and the like.

The storage unit 152 is a computer readable non-transitory recording medium, and may be a hard disk drive, an optical disk, or a flash memory, for example. The storage unit 152 stores an image processing program 152*a* that causes the processor 151 to perform a method for processing an image, which will be described later.

In the same manner as the learning support device 10, the learning support device 50 includes a processor 1, a storage unit 2, a memory 3, and an input/output unit 4. The storage unit 2 stores a learning support program that causes the processor 1 to perform the method for supporting learning according to the present embodiment, which will be described later. The method for supporting learning of the present embodiment is based on any one of the methods for supporting learning described in the first to fourth embodiments. Accordingly, the storage unit 2 stores any of data A1, A2, A3, . . . , B, I1, I2, I3, . . . , 6*a*, 6*b*, 6*c*, and 8 depending on the method for supporting learning of the present embodiment.

Next, the method for supporting learning that is performed by the learning support device 50 will be described by taking the method for supporting learning of the first embodiment as an example.

Figure 22A:
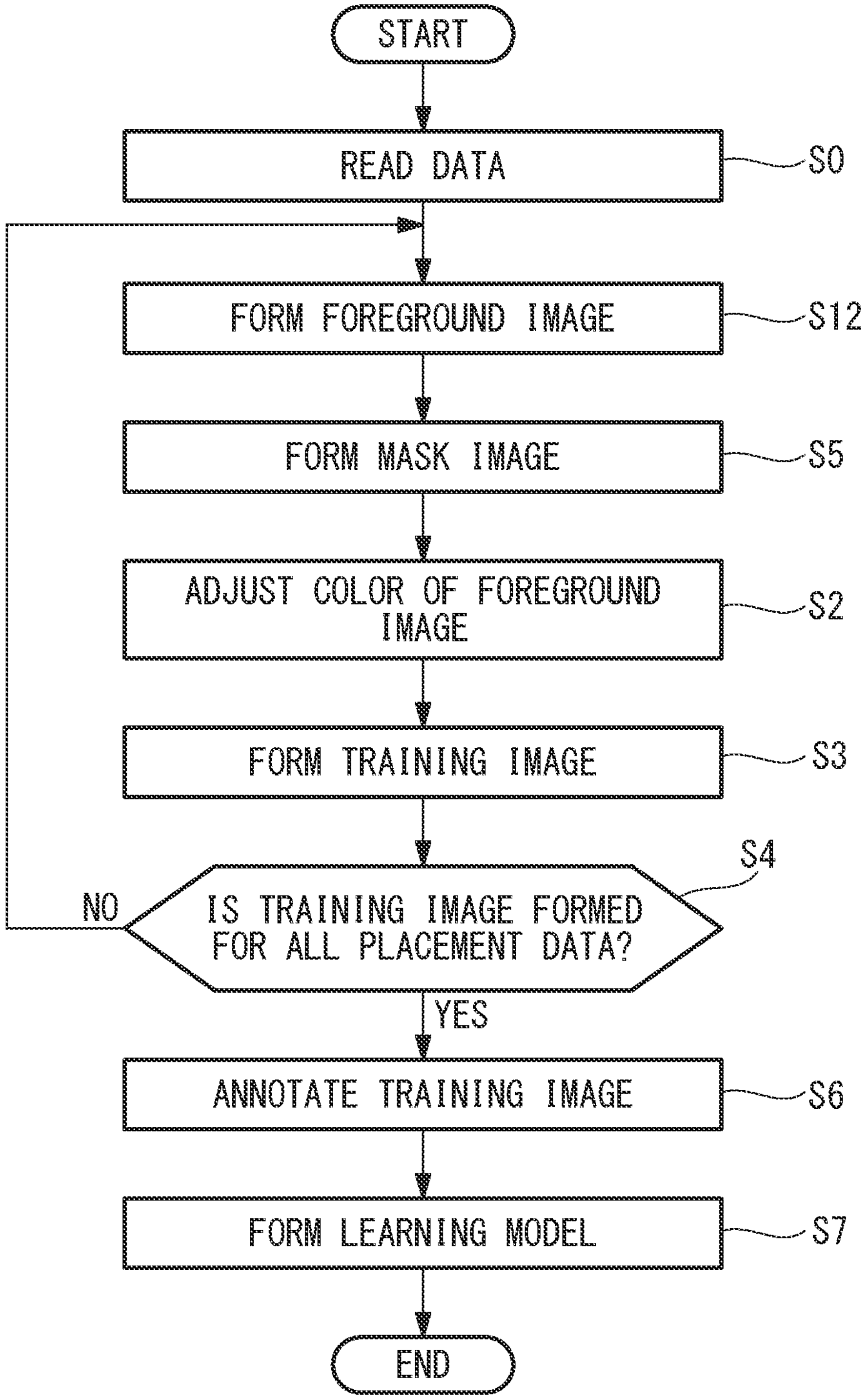
FIG. 22A is a flowchart of a method for supporting learning according to the fifth embodiment.

As shown in FIG. 22A, the method for supporting learning according to the present embodiment includes step S12 of forming a foreground image C, step S2 of adjusting the color of the foreground image C, step S3 of forming a training image D in which a foreground image C' is superimposed on a background image, step S5 of forming a mask image E based on the foreground image C, step S6 of annotating the training image D based on the mask image E, and step S7 of learning a plurality of training images D to form a learning model that recognizes treatment instruments within the endoscopic image G.

In step S12, the processor 1 forms a plurality of foreground images C having different brightness based on one set of placement data.

Figure 23:
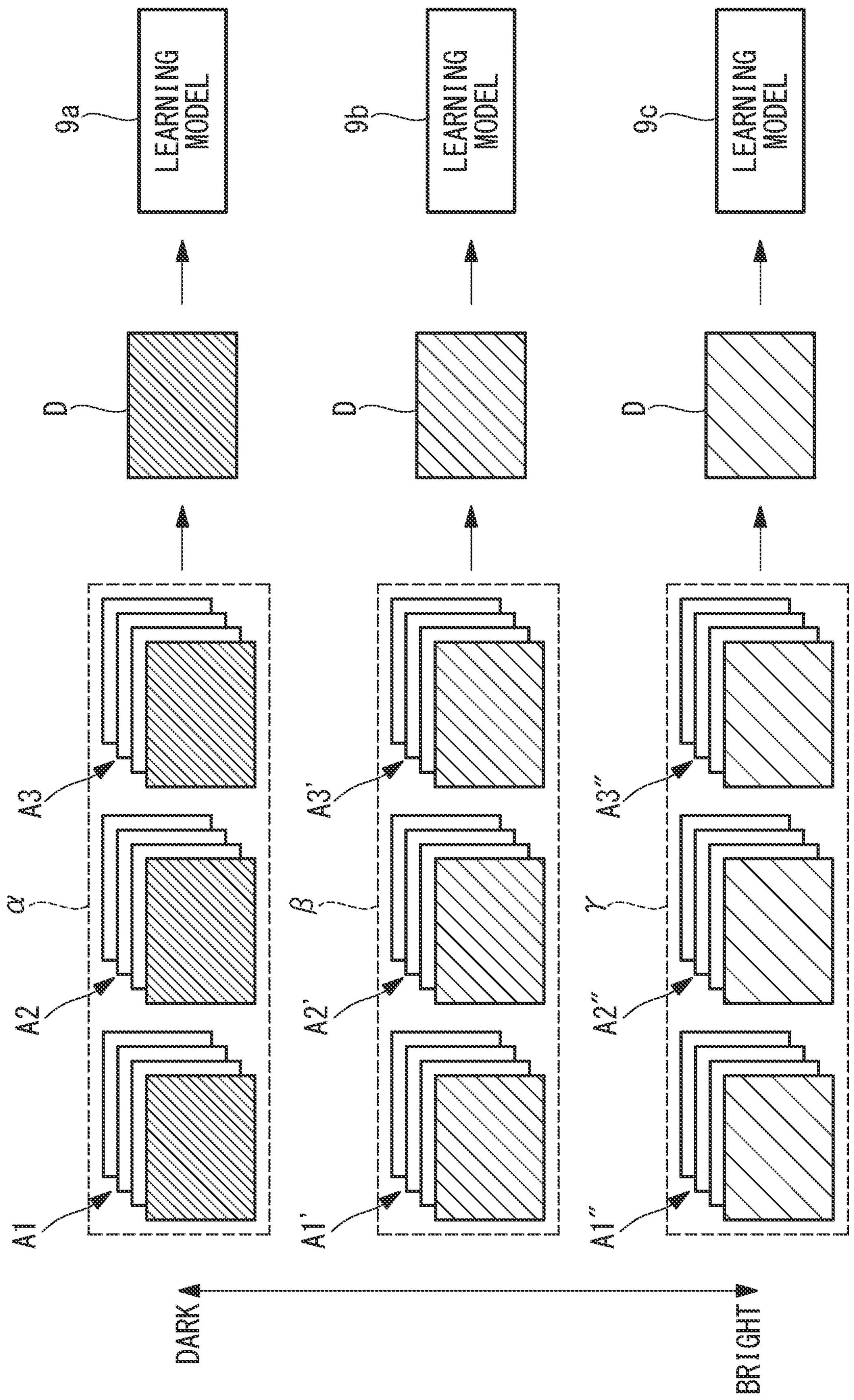
FIG. 23 is a diagram illustrating the method for supporting learning according to the fifth embodiment.

For example, as shown in FIG. 23, the storage unit 2 stores a plurality of sets a, B, y each of which is formed of a plurality of treatment instrument image groups. The plurality of sets a, B, Y correspond to brightness that differ from each other. For example, the set a is formed of treatment instrument image groups A1, A2, A3 each of which is formed of dark treatment instrument images, and the set y is formed of treatment instrument image groups A1 ", A2", A3" each of which is formed of bright treatment instrument images.

The processor 1 forms a foreground image C from each of the sets a, B, y, thus forming a plurality of foreground images C having the same number of treatment instruments and the same kind and placement, but different brightness, for each placement data 6.

In the following step S2, the processor 1 adjusts the colors of treatment instruments within each foreground image C.

In the following step S3, by superimposing each foreground image C' on a background image, the processor 1 forms a plurality of training images D having different brightness for one set of placement data 6.

Steps S4, S5, S6 are as described in the first embodiment.

After all training images D are annotated (step S6), the processor 1 learns a large number of training images D formed from the same set α, β or γ, thus forming a plurality of learning models 9*a*, 9*b*, 9*c* that correspond to different brightness of the endoscopic image (step S7). For example, the learning model 9*a* is for a dark endoscopic image G, and the learning model 9*c* is for a bright endoscopic image G. The learning models 9*a*, 9*b*, 9*c* are stored in the storage unit 2 of the learning support device 50.

Next, the method for processing an image that is performed by the image processing apparatus 15 during endoscopic surgery will be described.

Figure 22B:
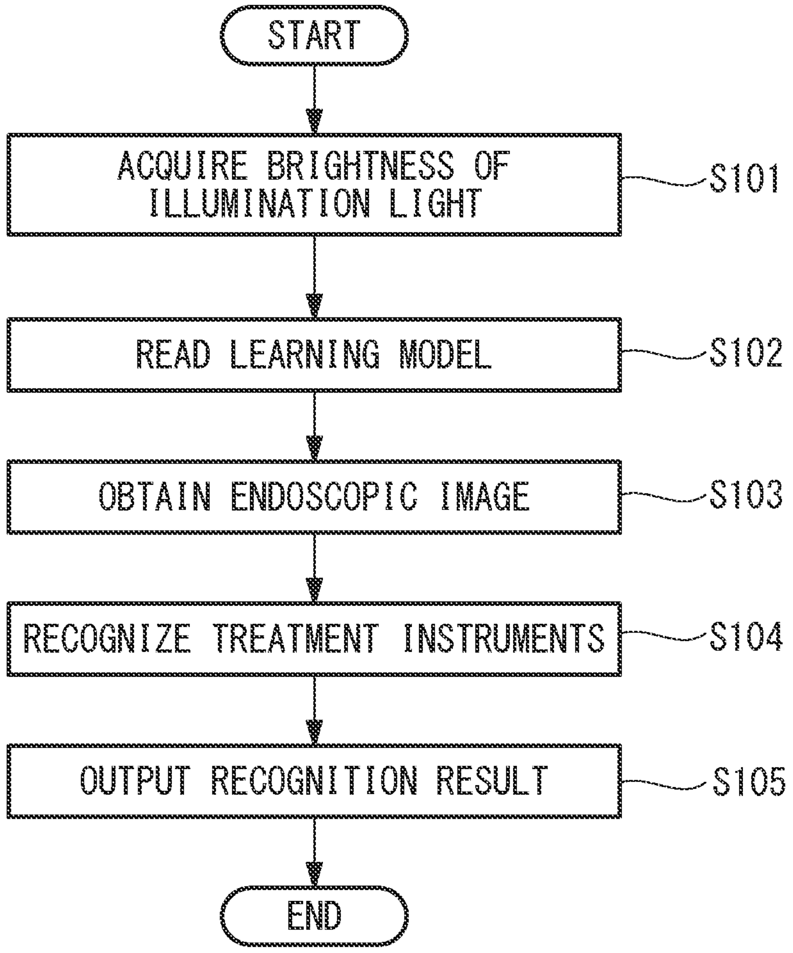
FIG. 22B is a flowchart of a method for processing an image according to the fifth embodiment.

As shown in FIG. 22B, the method for processing an image according to the present embodiment includes step S101 of acquiring information on the luminance of the illumination light L from the light source device 17, step S102 of reading a learning model from the learning support device 50 based on the luminance, step S103 of obtaining an endoscopic image G, step S104 of recognizing treatment instruments within the endoscopic image G based on the learning model, and step S105 of outputting a recognition result to the display device 14.

During endoscopic surgery, the endoscopic image G is sequentially input to the image processing apparatus 15 from the endoscope 11.

The processor 151 obtains a current set value of the luminance of the illumination light L from the light source device 17 (step S101), and reads the learning model 9*a*, 9*b* or 9*c* that corresponds to the set value from the learning support device 50 (step S102).

Next, the processor 151 obtains the endoscopic image G that is input to the image processing apparatus 15 (step S103), and inputs the endoscopic image G to the read learning model to obtain the positions of the regions of recognized treatment instruments as the recognition result from the learning model (step S104).

Figure 24:
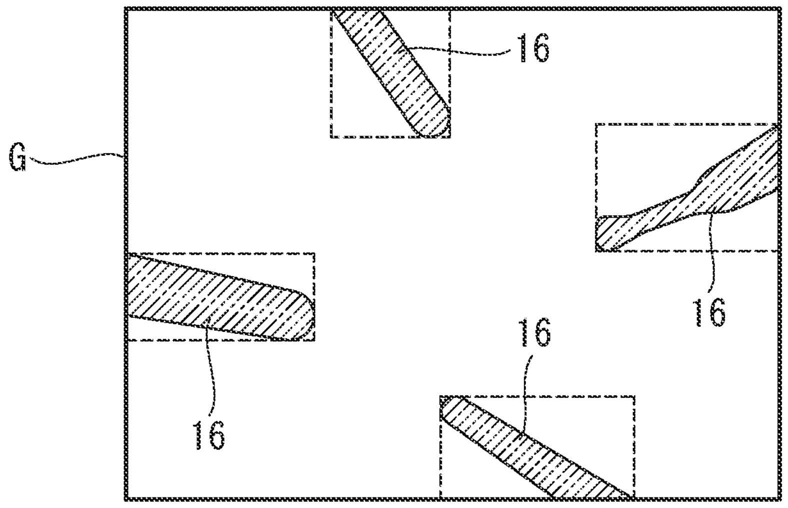
FIG. 24 is a diagram showing an example of a recognition result with respect to treatment instruments that is displayed on a display device.

The processor 151 displays the recognition result with respect to the treatment instruments on the display device 14 (step S105). For example, as shown in FIG. 24, the processor 151 may superimpose color markers on the regions of the recognized treatment instruments 16 within the endoscopic image G, or may superimpose frames that surround the recognized treatment instruments 16 on the endoscopic image G.

The recognition result with respect to the treatment instruments may be used for tracking control performed by the control device 13.

According to the present embodiment, as described in the first to fourth embodiments, the training image D is an image with reality, that is, an image in which the placement and the colors of the treatment instruments are close to those in the clinical image and hence, a learning model formed by learning such a training image D has high recognition accuracy for treatment instruments within the clinical image. Accordingly, it is possible to enhance recognition performance for treatment instruments within the endoscopic image G during endoscopic surgery. Thus, it is possible to cause the field of view of the endoscope 11 to stably track the treatment instruments during tracking control and hence, a more comfortable field of view can be provided to a user, such as an operator or an assistant.

The brightness of the endoscopic image G varies depending on the luminance of the illumination light L. According to the present embodiment, a learning model corresponding to the luminance of the illumination light L is used for recognition of treatment instruments. For example, when the illumination light L is dark, a learning model for a dark endoscopic image G that is formed by learning a dark training image D is used. Thus, it is possible to further enhance recognition accuracy for treatment instruments within the endoscopic image G.

In step S104 in the present embodiment, the processor 151 may correct the endoscopic image G such that the endoscopic image G approaches the training image D (step S104*a*), and the processor 151 may input the corrected endoscopic image G to the learning model (step S104*b*).

Figure 25:
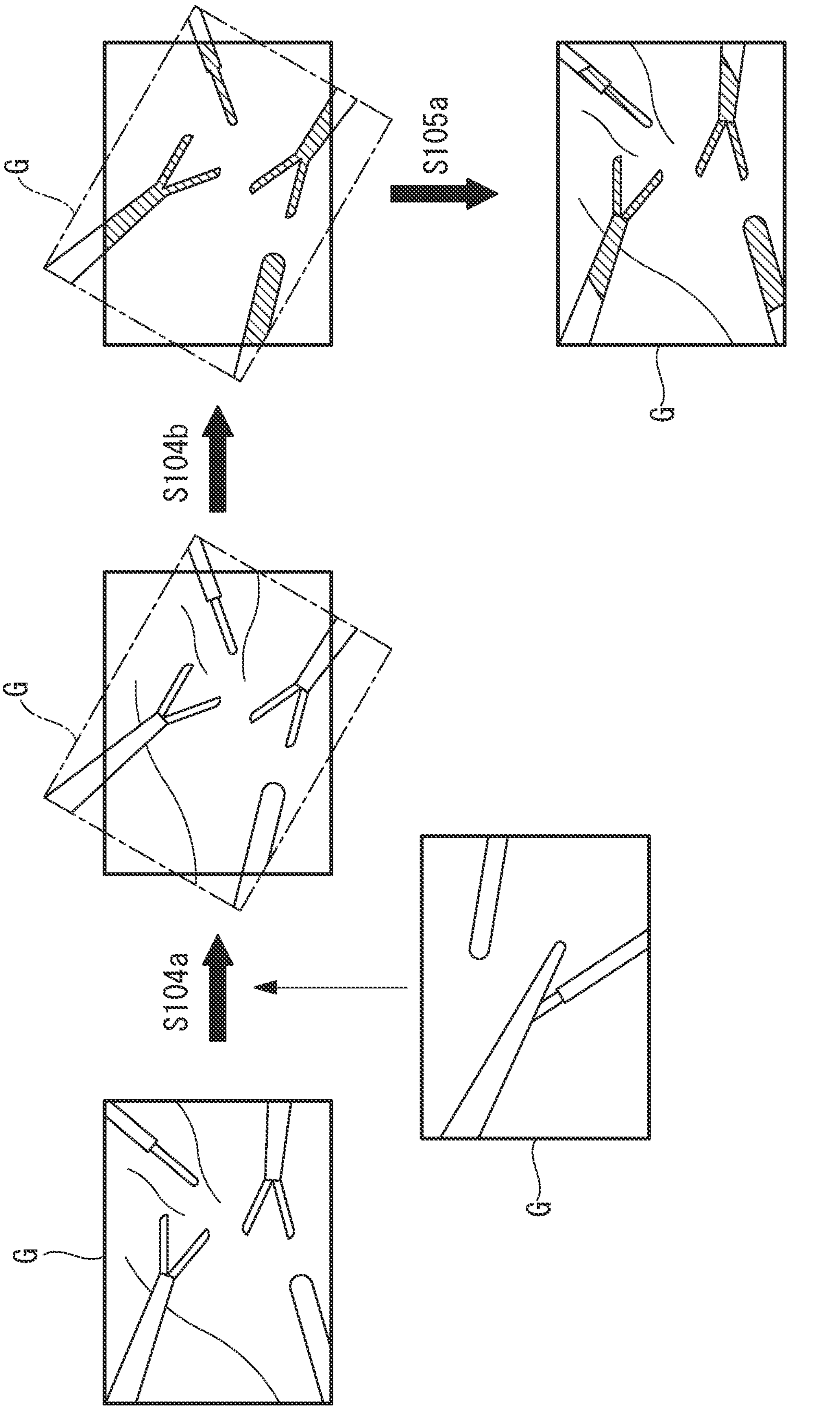
FIG. 25 is a diagram illustrating correction of an endoscopic image based on a training image.

To be more specific, as shown in FIG. 25, the processor 151 corrects at least one of hue, saturation, or a rotation angle of the endoscopic image G to cause how the treatment instruments appear in the endoscopic image G to approach how the treatment instruments appear in the training image D. The training image D is any one of the plurality of training images D used for formation of the learning model.

As described above, the placement of treatment instruments within the endoscopic image G is roughly determined by a surgical method. However, the positions of treatment instruments within the endoscopic image G may be displaced in a circumferential direction depending on the orientation of the endoscope 11, for example. By rotating the endoscopic image G such that the placement of treatment instruments within the endoscopic image G approaches the placement of treatment instruments within the training image D, and by inputting the rotated endoscopic image G to the learning model, it is possible to enhance recognition accuracy for treatment instruments.

Hue and saturation of treatment instruments within the endoscopic image G may differ from hue and saturation of treatment instruments within the training image D. By correcting hue and saturation of treatment instruments within the endoscopic image G such that the hue and saturation of the treatment instruments within the endoscopic image G approach hue and saturation of treatment instruments within the training image D, and by inputting the corrected endoscopic image G to the learning model, it is possible to enhance recognition performance.

In step S105, the processor 151 may reversely rotate the recognition result (step S105*a*) and, thereafter, may display the recognition result on the display device 14 in a state in which the recognition result is superimposed on the endoscopic image G.

In the present embodiment, the processor 1 forms a plurality of training images D that differ from each other in brightness from the plurality of sets a, B, y each of which is formed of treatment instrument image groups. However, the processor 1 may form a plurality of training images D by using another method.

For example, the processor 1 may form, from one foreground image C, a plurality of foreground images having different brightness by performing image processing, and may form a plurality of training images D from the plurality of foreground images.

In the present embodiment, the learning support device 50 is separated from the control device 13 and the image processing apparatus 15. However, instead of adopting such a configuration, the learning support device 50 may be integrally formed with at least one of the control device 13 or the image processing apparatus 15. For example, the learning support device 50 and the image processing apparatus 15 may be incorporated in the control device 13.

The embodiments of the present invention and modifications of the embodiments have been described heretofore. However, the present invention is not limited to the above, and may be suitably modified without departing from the gist of the present invention.

In each of the above-mentioned embodiments and the modifications, the sample image group is formed of the treatment instrument image groups A1, A2, A3, . . . and the background image group B. However, the sample image group may further include an image group of another object. Another object may be an artifact such as gauze or a Nelaton tube, or an organ, for example.

REFERENCE SIGNS LIST

10, 20, 30, 40, 50 learning support device
1 processor
2 storage unit
3 memory
4 input/output unit
5*a*, 5*b*, 5*c*, 5*d*, 5*e* learning support program
6*a*, 6*b*, 6*c*, 6*d* placement data
7 learning-use model
8 numerical formula model
11 endoscope
15 image processing apparatus
100 endoscope system
A1, A2, A3 treatment instrument image group
B background image group
C, C' foreground image
D training image
E mask image
I1, I2, I3 CAD data
G endoscopic image
L illumination light

What is claimed is:

1. A learning support device that supports formation of a learning model that recognizes a treatment instrument within an endoscopic image, the learning support device comprising a processor and a storage unit configured to store a learning-use model, wherein the processor is configured to:

generate a foreground image including at least one treatment instrument by placing an image of the at least one treatment instrument within an image region based on placement data, the placement data being data showing a three-dimensional placement of the at least one treatment instrument as viewed through an endoscope;

form a training image by superimposing the foreground image on a background image;

cause the learning-use model to learn the training image to generate the learning model that recognizes the treatment instrument within the endoscopic image;

generate a plurality of training images that differ from each other in brightness, the plurality of training images including the training image; and cause the learning-use model to learn the plurality of training images to generate a plurality of learning models that correspond to different brightness of the endoscopic image.

2. The learning support device according to claim 1, wherein the placement data includes at least one of:

the number of treatment instruments within the endoscopic image;

positions of a distal end and a proximal end of each of the at least one treatment instrument within the endoscopic image, an area of each of the at least one treatment instrument within the endoscopic image; or a three-dimensional position and orientation of each of the at least one treatment instrument as viewed through the endoscope.

3. The learning support device according to claim 1, wherein the placement data includes distance information relating to at least one distance between the endoscope and each of the at least one treatment instrument, the processor is further configured to:

adjust at least one of saturation, hue, or brightness of each of the at least one treatment instrument within the foreground image based on the distance information; and generate the training image by superimposing the foreground image, which is adjusted, on the background image.

4. The learning support device according to claim 1, wherein the processor is further configured to:

correct brightness of each of the at least one treatment instrument within the foreground image based on at least one (i) a three-dimensional position and orientation of each of the at least one treatment instrument as viewed through the endoscope, and (ii) a spatial distribution of luminance of illumination light of the endoscope; and generate the training image by superimposing the foreground image, which is corrected, on the background image.

5. The learning support device according to claim 1, wherein the processor is further configured to:

adjust brightness of each of the at least one treatment instrument based on a brightness distribution of the background image, and generate the training image by superimposing the foreground image, which is adjusted, on the background image.

6. The learning support device according to claim 1, wherein the processor is further configured to:

generate a mask image obtained by extracting only a region of the at least one treatment instrument within the foreground image; and annotate the region of the at least one treatment instrument within the training image based on the mask image.

7. An endoscope system comprising:

the learning support device according to claim 1;

an endoscope configured to acquire the endoscopic image; and an image processing apparatus including a processor and a storage unit configured to store the learning model, wherein the processor of the image processing apparatus is configured to:

input the endoscopic image to the learning model; and obtain, from the learning model, a recognition result with respect to the treatment instrument within the endoscopic image.

8. The endoscope system according to claim 7, wherein the processor of the image processing apparatus is further configured to:

correct at least one of hue, saturation, or a rotation angle of the endoscopic image based on the training image used for formation of the learning model; and input the endoscopic image, which is corrected, to the learning model to recognize the treatment instrument within the endoscopic image.

9. The endoscope system according to claim 7, further comprising a display device, wherein the processor of the image processing apparatus is further configured to display the recognition result on the display device.

10. A method for supporting learning, the method supporting formation of a learning model that recognizes a treatment instrument within an endoscopic image, the method comprising:

generating a foreground image including at least one treatment instrument by placing an image of the at least one treatment instrument within an image region based on placement data, the placement data being data showing a three-dimensional placement of the at least one treatment instrument as viewed through an endoscope;

generating a training image by superimposing the foreground image on a background image;

causing a learning-use model to learn the training image to generate the learning model that recognizes the treatment instrument within the endoscopic image;

generating a plurality of training images that differ from each other in brightness, the plurality of training images including the training image; and causing the learning-use model to learn the plurality of training images to generate a plurality of learning models that correspond to different brightness of the endoscopic image.

11. A computer readable non-transitory recording medium that stores a learning support program that causes a computer to perform the method for supporting learning according to claim 10.

12. An endoscope system comprising:

a learning support device that supports formation of a learning model that recognizes a treatment instrument within an endoscopic image, the learning support device comprising a processor and a storage unit configured to store a learning-use model;

an endoscope configured to acquire the endoscopic image; and an image processing apparatus including a processor and a storage unit configured to store the learning model, wherein the processor of the learning support device is configured to:

generate a foreground image including at least one treatment instrument by placing an image of the at least one treatment instrument within an image region based on placement data, the placement data being data showing a three-dimensional placement of the at least one treatment instrument as viewed through an endoscope;

form a training image by superimposing the foreground image on a background image; and cause the learning-use model to learn the training image to generate the learning model that recognizes the treatment instrument within the endoscopic image; and wherein the processor of the image processing apparatus is configured to:

input the endoscopic image to the learning model;

obtain, from the learning model, a recognition result with respect to the treatment instrument within the endoscopic image;

correct at least one of hue, saturation, or a rotation angle of the endoscopic image based on the training image used for formation of the learning model; and input the endoscopic image, which is corrected, to the learning model to recognize the treatment instrument within the endoscopic image.

* * * * *